(12) United States Patent
Moberg et al.

(10) Patent No.: US 7,494,481 B2
(45) Date of Patent: Feb. 24, 2009

(54) MULTI-POSITION INFUSION SET DEVICE AND PROCESS

(75) Inventors: Sheldon B. Moberg, Thousand Oaks, CA (US); Mark D. Holt, Moorpark, CA (US); Albert D. Candioty, Agoura Hills, CA (US); Milad T. Girgis, North Hills, CA (US); Julian D. Kavazov, Arcadia, CA (US); Philip J. Hudak, Thousand Oaks, CA (US); Frederick C. Houghton, Moorpark, CA (US); Sean M. Collins, Canyon Country, CA (US); Lance E. Shelter, Downey, CA (US); Jason Adams, Frisco, TX (US); Clint Taylor, Addison, CA (US); Brian Highley, Keller, TX (US); Kraig P. Kooiman, Flower Mound, TX (US); Tommy Cushing, McKinney, TX (US)

(73) Assignee: Medtronic Minimed, Inc., Northridge, CA (US)

( * ) Notice: Subject to any disclaimer, the term of this patent is extended or adjusted under 35 U.S.C. 154(b) by 0 days.

(21) Appl. No.: 11/004,594

(22) Filed: Dec. 3, 2004

(65) Prior Publication Data
US 2006/0129090 A1 Jun. 15, 2006

(51) Int. Cl.
*A61M 5/32* (2006.01)
(52) U.S. Cl. .................. 604/174; 604/164.01
(58) Field of Classification Search .......... 604/535, 604/93.01, 164.01, 29, 533, 539, 263, 174, 604/178, 180, 177
See application file for complete search history.

(56) References Cited

U.S. PATENT DOCUMENTS

| | | | |
|---|---|---|---|
| 4,601,708 A | 7/1986 | Jordan | |
| 4,645,495 A | 2/1987 | Vaillancourt | |
| 4,685,903 A | 8/1987 | Cable et al. | |
| 4,743,231 A | 5/1988 | Kay et al. | |
| 4,755,173 A | 7/1988 | Konopka et al. | |
| 4,787,891 A | 11/1988 | Levin et al. | |

(Continued)

FOREIGN PATENT DOCUMENTS

EP 1 421 968 A2 5/2004

OTHER PUBLICATIONS

PCT International Search Report/Written Opinion dated Apr. 13, 2006 for PCT/US2005/041006.

*Primary Examiner*—Nicholas D Lucchesi
*Assistant Examiner*—Christopher D Koharski
(74) *Attorney, Agent, or Firm*—Foley & Lardner LLP

(57) ABSTRACT

An infusion set for subcutaneous delivery of an infusant. The infusion set may include a base removably attachable to an infusion site and a connector temporarily lockable to the base. The connector can engage the base in a plurality of orientations. The connector locks into the base after at least partial rotation of the connector about the base. The connector may include flexible arms which unlock the connector from the base. The base includes a cannula for insertion through the infusion site. The connector includes a tubing for passing the infusant. The infusant is subcutaneously passable from the tubing through the cannula when the connector is attached to the base. The infusion set may also include a hub removably attachable to the base that includes a needle that extends through the base and the cannula and a guard removably attachable to the base opposite the hub for surrounding the needle.

67 Claims, 20 Drawing Sheets

U.S. PATENT DOCUMENTS

| | | |
|---|---|---|
| 4,813,939 A | 3/1989 | Marcus |
| 4,955,861 A | 9/1990 | Enegren et al. |
| 4,966,589 A | 10/1990 | Kaufman |
| 4,988,339 A | 1/1991 | Vadher |
| 4,994,042 A | 2/1991 | Vadher |
| 5,122,119 A | 6/1992 | Lucas |
| 5,147,375 A | 9/1992 | Sullivan |
| 5,176,662 A | 1/1993 | Bartholomew et al. |
| 5,257,980 A | 11/1993 | Van Antwerp et al. |
| 5,368,045 A | 11/1994 | Clement et al. |
| 5,390,671 A | 2/1995 | Lord et al. |
| 5,522,803 A | 6/1996 | Teissen-Simony |
| 5,545,143 A | 8/1996 | Fischell |
| 5,545,152 A | 8/1996 | Funderburk et al. |
| 5,562,631 A | 10/1996 | Bogert |
| 5,568,806 A | 10/1996 | Cheney, II et al. |
| 5,584,813 A | 12/1996 | Livingston et al. |
| 5,586,553 A | 12/1996 | Halili et al. |
| 5,591,188 A | 1/1997 | Waisman |
| 5,607,407 A | 3/1997 | Tolkoff et al. |
| 5,779,665 A | 7/1998 | Mastrototaro et al. |
| 5,851,197 A | 12/1998 | Marano et al. |
| 5,868,711 A | 2/1999 | Kramer et al. |
| 5,957,895 A | 9/1999 | Sage et al. |
| 5,968,011 A | 10/1999 | Larsen et al. |
| 5,980,506 A | 11/1999 | Mathiasen |
| 6,017,328 A | 1/2000 | Fischell et al. |
| 6,093,172 A | 7/2000 | Funderburk et al. |
| 6,123,690 A | 9/2000 | Mejslov |
| 6,290,677 B1 | 9/2001 | Arai et al. |
| 6,293,925 B1 | 9/2001 | Safabash et al. |
| 6,302,866 B1 | 10/2001 | Marggi |
| 6,355,021 B1 | 3/2002 | Nielsen et al. |
| 6,461,329 B1 | 10/2002 | Van Antwerp et al. |
| 6,572,586 B1 | 6/2003 | Wojcik |
| 6,579,265 B1 | 6/2003 | Kihara et al. |
| 6,579,267 B2 | 6/2003 | Lynch et al. |
| 6,685,674 B2 | 2/2004 | Douglas et al. |
| 6,736,797 B1 | 5/2004 | Larsen et al. |
| 6,923,791 B2 | 8/2005 | Douglas |
| 2002/0022855 A1 | 2/2002 | Bobroff et al. |
| 2002/0072720 A1 | 6/2002 | Hague et al. |
| 2002/0119711 A1 | 8/2002 | Van Antwerp et al. |
| 2004/0138620 A1 | 7/2004 | Douglas et al. |
| 2004/0260235 A1* | 12/2004 | Douglas ................ 604/93.01 |
| 2005/0020972 A1* | 1/2005 | Horisberger et al. ..... 604/93.01 |
| 2005/0101910 A1* | 5/2005 | Bowman et al. ......... 604/93.01 |
| 2005/0101933 A1* | 5/2005 | Marrs et al. ................. 604/506 |
| 2005/0107746 A1 | 5/2005 | Pajunk et al. |
| 2005/0113761 A1 | 5/2005 | Faust et al. |

\* cited by examiner

MULTI-POSITION INFUSION SET DEVICE AND PROCESS

BACKGROUND

1. Field of the Invention

The present invention relates to infusion sets and, in particular, to infusion sets having a cannula which is inserted into the skin of a patient to facilitate the subcutaneous transfer of an infusant.

2. Description of Related Art

Infusion sets are typically used for delivering a fluid, drug or other infusant to a subcutaneous location in a patient. While most infusion sets include a delivery tube connected to an infusion pump or other fluid or drug delivering device, the configuration of some infusion sets have been disadvantageous to patients for a variety of reasons.

If an infusion set includes a base portion disposed on the skin of a patient and a connector portion that attaches to the base portion, a delivery tube may be attached to the connector portion. Thus, when the connector portion is attached to the base portion, the delivery tube may be connected to an infusion pump or other device for fluid delivery, permitting the patient to administer the desired or necessary infusant. However, if the connector portion of the infusion set is positioned in such a manner that the delivery tube is in a position that is undesirable or impractical for the patient, the patient is resigned to removing the base portion from the patient's skin and inserting a new infusion set base, since the old one cannot be safely reused. It is not normally possible to re-orient the base portion because re-orienting the base portion typically includes re-inserting a needle into the skin. Also, re-orienting the base portion can be discomforting, painful or could lead to infection and thus is undesirable for the patient.

Some infusion sets are configured so that the connector portion and, thus, the delivery tube, may rotate freely about the base portion. Freely rotating infusion sets have disadvantages. Generally, too much movement of the delivery tube is undesirable. For example, because the delivery tube is typically delivering a fluid or some type of drug or infusant to a patient, it is necessary that the fluid path remain unobstructed. If the delivery tube is permitted to rotate freely around the base portion of the infusion set, the delivery tube may be subject to entanglement, twisting, kinking or the like, interrupting the infusion process. In addition, a freely rotating delivery tube can, at times, appear or feel to the patient to be disconnected from the patient and, thus, may result in a sense of insecurity for the patient.

The needs of patients who rely on infusion sets are numerous. For example, patients need infusion sets that require a positive action for releasing a connector from a base—infusion sets that release inadvertently are inconvenient and worrisome. In addition, while it is desirable that the size of the infusion set be minimized, it is also desirable that a patient be able to hold on to the infusion set and that protective pieces of the infusion set remain in place when the infusion set is in storage. Moreover, patients desire the flexibility to attach a connector to a base in multiple positions but also a connector that maintains the position of a delivery tube so that the aforementioned problems of a freely rotating tube are avoided.

SUMMARY

According to an embodiment of the present invention, an infusion set may include a base removably attachable to an infusion site for providing a subcutaneous path for an infusant and a connector temporarily lockable to the base. The base may be engagable by the connector in a plurality of orientations. In addition, the base may include a plurality of apertures and the connector may include a plurality of tabs insertable into the plurality of apertures.

The connector may be at least partially rotatable about the base and at least one tab of the plurality of tabs may be rotatable from a position within at least one aperture of the plurality of apertures to a locked position. The base may include at least one abutment for locking at least one tab of the plurality of tabs into a position. The connector may include a plurality of arms and each arm of the plurality of arms may be fixedly attached to a tab of the plurality of tabs. The plurality of arms may be flexible. Each arm of the plurality of arms may be flexed to remove a tab of the plurality of tabs from a locked position to an unlocked position. The connector may be removable from the base by simultaneously flexing the plurality of arms.

According to an embodiment of the present invention, the base may include a cannula for insertion through the infusion site. The connector may include a tubing for passing the infusant. The infusant may be subcutaneously passable from the tubing through the cannula when the connector is attached to the base.

Embodiments of the invention may include a hub removably attachable to the base. The hub may include a needle extending through the base and through the cannula. Embodiments of the invention may also include a guard removably attachable to the base opposite the hub for surrounding the needle. The needle may be subcutaneously insertable into the infusion site for subcutaneously positioning the cannula.

The base may include an adhesive pad for attaching to the infusion site. The infusion site may be the skin of a patient.

According to an embodiment of the present invention, a method for delivering an infusant may include positioning a base at an infusion site for providing a subcutaneous path for the infusant; engaging the base with a connector, the connector being temporarily lockable to the base; and rotating, at least partially, the connector about the base until the connector temporarily locks to the base. The base may be engagable by the connector in a plurality of orientations. The base may include a plurality of apertures and the connector may include a plurality of tabs. The method may further include inserting the plurality of tabs into the plurality of apertures. The method may further include providing at least one abutment on the base for locking at least one tab of the plurality of tabs in the locked position and may further include providing a plurality of arms on the connector. Each arm of the plurality of arms may be fixedly attached to a tab of the plurality of tabs. The plurality of arms may be flexible and the method may further include flexing each arm of the plurality of arms to remove a tab of the plurality of tabs from a locked position to an unlocked position. The method may further include simultaneously flexing the plurality of arms to remove the connector from the base and inserting a cannula connected to the base through the infusion site.

The method may further include providing a hub removably attachable to the base, the hub including a needle extending through the base and through the cannula; providing a guard removably attachable to the base opposite the hub for surrounding the needle; and subcutaneously inserting the needle into the infusion site for subcutaneously positioning the cannula.

According to an embodiment of the present invention, an infusion set may include a base removably attachable to an infusion site for providing a subcutaneous path for an infusant; a connector removably attachable to the base; and a locking mechanism for temporarily locking the connector to the base. The base may be engagable by the connector in a plurality of orientations. The base may include a plurality of apertures.

BRIEF DESCRIPTION OF THE DRAWINGS

A detailed description of embodiments of the invention will be made with reference to the accompanying drawings, wherein like numerals designate corresponding parts in the several figures.

DETAILED DESCRIPTION

In the following description of preferred embodiments, reference is made to the accompanying drawings which form a part hereof, and in which is shown by way of illustration specific embodiments in which the invention may be practiced. It is to be understood that other embodiments may be utilized and structural changes may be made without departing from the scope of the preferred embodiments of the present invention.

Embodiments of the present invention relate to infusions sets and processes of using and making same. Such infusion sets may be employed to transfer a medication, an infusant and the like between a reservoir and a patient. For example, an infusion set may be used by connecting the infusion set to an insulin infusion pump to a diabetic patient. Other embodiments may be employed for other medical or infusion applications or procedures.

Figure 1:
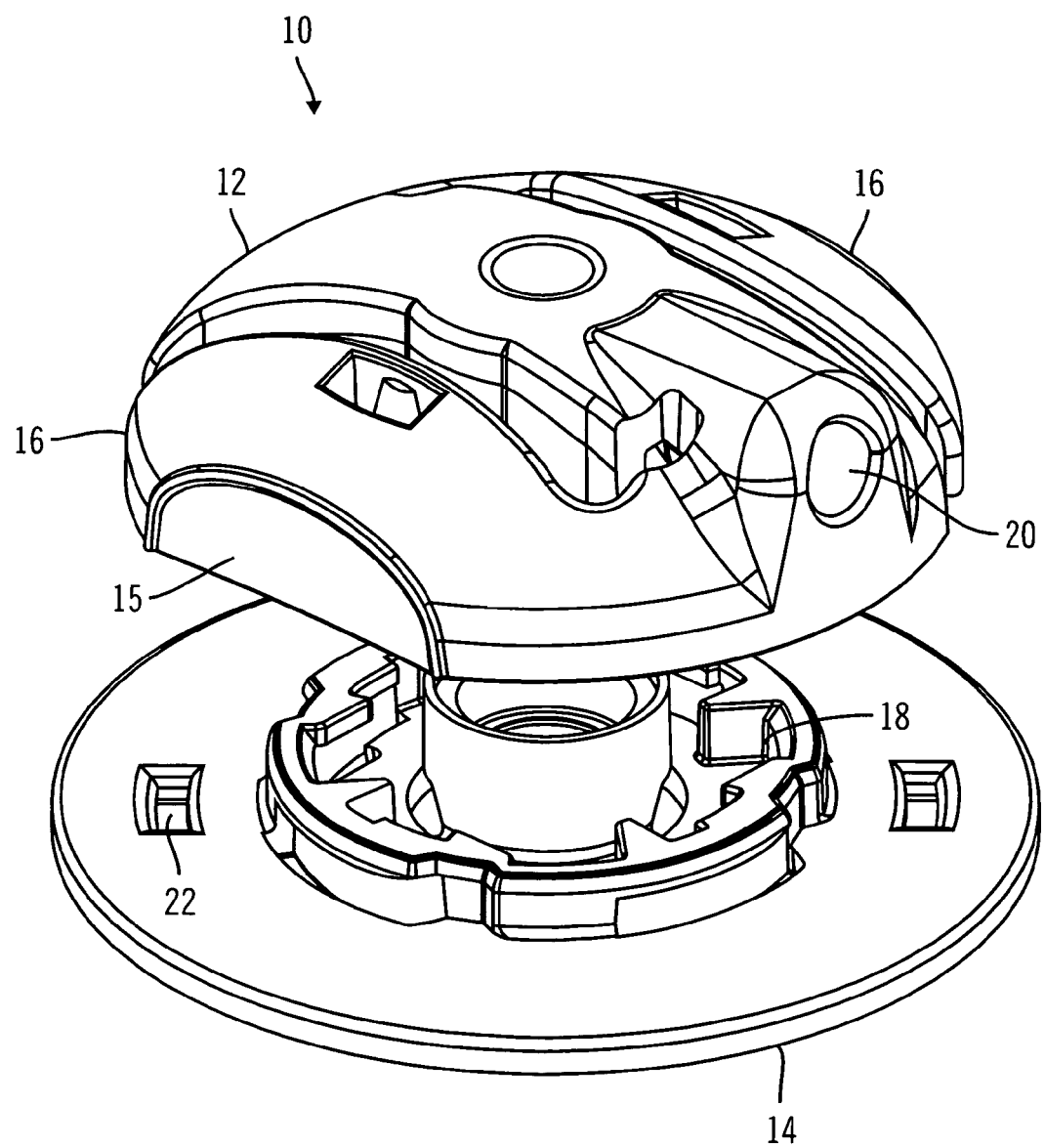
FIG. 1 shows a perspective view of an infusion set according to an embodiment of the present invention.

FIG. 1 shows an infusion set 10 according to an embodiment of the present invention. The embodiment of the infusion set 10 shown in FIG. 1 includes, but is not limited to, a connector 12 and a base 14. The connector 12 and the base 14 in the embodiment of the invention shown in FIG. 1 are configured such that the connector 12 is removably attachable to the base 14.

The connector 12 may include, without limitation, two or more arms 16 that may be used to facilitate connecting and/or removing the connector 12 to the base 14. In addition, the arms 16 may include a cutout, depression or surface 15 that may aid a user or patient in gripping the connector 12. The connector 12 may also include a port 20 to which is connected a tubing (not shown) for passing a fluid, medication or other infusant from an infusion pump, reservoir or the like through the infusion set to a subcutaneous location in a patient.

The base 14 may include a plurality of grooves, cutouts, depressions, spacings, apertures and the like to facilitate a connection between the connector 12 and the base 14 as will be explained in greater detail below. For example, as can be seen in the embodiment of the invention shown in FIG. 1, the base 14 includes an inner depression 18 for accepting a tab or other extended member disposed on the connector 12 as well as an aperture 22 for accepting a tab or other extended member disposed on a hub, as will be explained in greater detail below.

In the embodiment of the invention shown in FIG. 1, the connector 12 and the base 14 are of a substantially circular disc shape. However, the connector 12 and the base 14 need not be circular and could be designed to be any shape convenient to or desired by a patient, healthcare professional or other user of the infusion set. In addition, the connector 12 and the base 14 may be designed in a variety of sizes. For example, according to an embodiment of the present invention, the connector 12 and the base 14 may be designed small enough to be unobtrusive to a patient when wearing the infusion set 10 but large enough so that the patient can easily hold onto the infusion set 10 when applying the infusion set 10 to or removing the infusion set 10 from the patient's skin. For example, the connector and base may have a circular disc shape with a diameter in the range of about 0.5 inches (1.27 cm.) to about 1.25 inches (3.175 cm.).

Also, according to an embodiment of the present invention, the base 14 may be designed so that it can be affixed to a patient's skin. For example, the base 14 may include an adhesive applied to a bottom portion of the base 14, i.e., the portion of the base 14 that comes into contact with a patient's skin, so that the base 14 adheres to the patient's skin when applied. According to another embodiment of the present invention, the base 14 may be supplied with an adhesive pad attached to a portion of the base 14, such as a bottom portion, for example, which may adhere to the patient's skin when applied.

Figure 2:
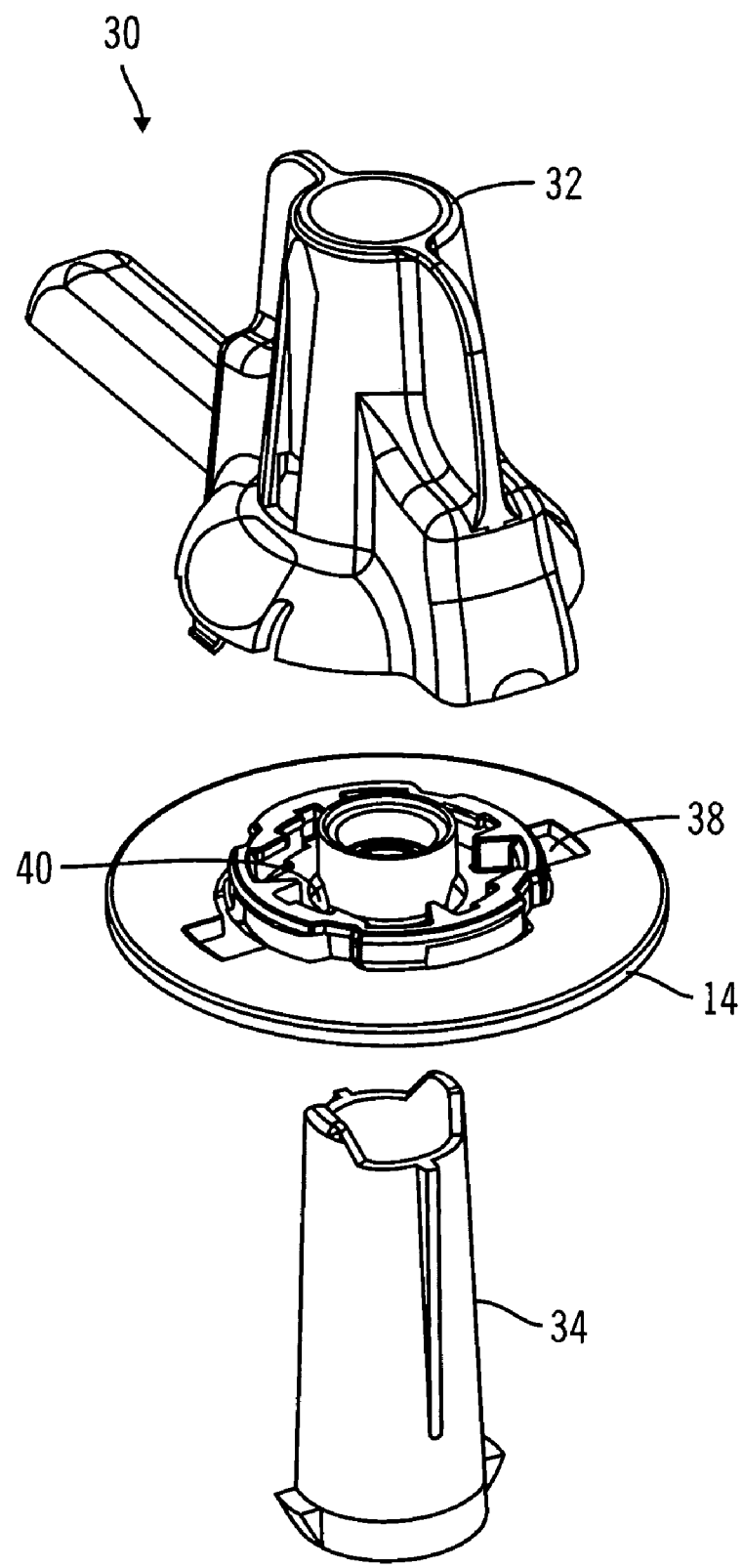
FIG. 2 shows a perspective view of an infusion set according to another embodiment of the present invention.

FIG. 2 shows an infusion set 30 according to another embodiment of the present invention. The infusion set 30 shown in FIG. 2 includes, without limitation, a hub 32, a base 14 and a guard 34. Whereas the embodiment of the infusion set shown in FIG. 1 may be used during operation with a patient, the embodiment of the invention shown in FIG. 2 may be used during storage. As will be explained in greater detail below, the hub 32 affixes to a top or first side of the base 14 via a hub aperture 38. In addition, the guard 34 attaches to a bottom or second side of the base 14 via the guard apertures 40. The hub 32 may be used to cover the base 14 and to facilitate application of the base 14 onto the skin of a patient. The guard 34 may be used as a protective element to cover a needle (not shown) or other protrusion that may extend through the bottom of the base 14.

According to an embodiment of the present invention, the base 14 may be designed in a variety of ways. For example, the base 14 may be designed with sufficient size and shape so that it is manageable, for example, easy to grip and maneuver, for a patient or other user when applying the base 14 to a patient's skin. According to an embodiment of the present invention, the base 14 may be designed large enough so that a patient may secure the base 14 with his or her fingers when removing the hub 32 from the base 14.

The embodiments of the infusion sets shown in FIGS. 1 and 2 may be made from a variety of materials. For example, according to embodiments of the present invention, the connector 12, base 14, hub 32 and guard 34 of the infusions sets shown in FIGS. 1 and 2 may be made from plastics, such as PVC, polypropylene, polycarbonate and the like, for example, suitable rubbers, polymers, other synthetic materials and the like or combinations of two or more of these materials used together on a single part utilizing processes such as over molding or two-shot molding.

Figure 3:
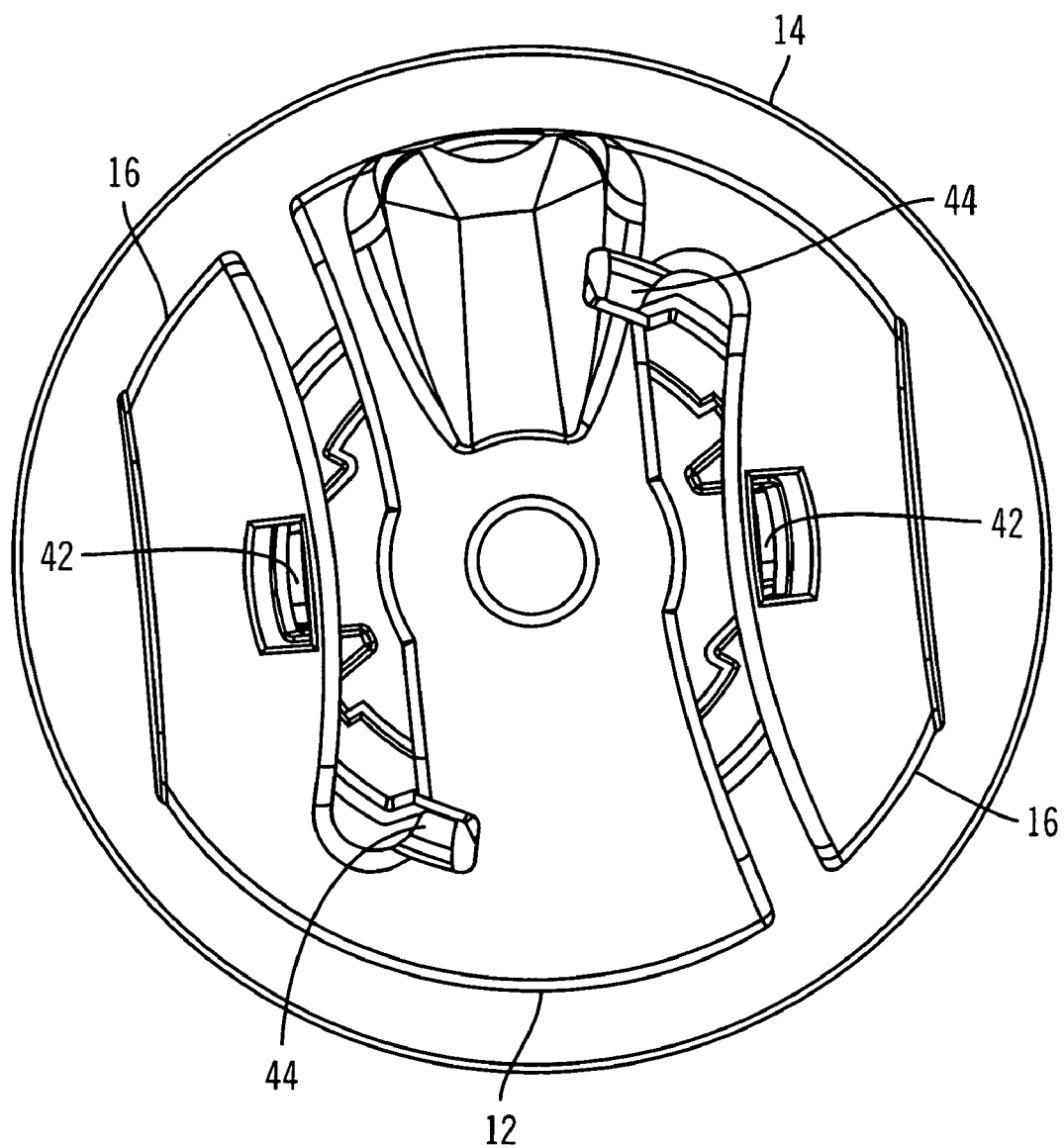
FIG. 3 shows a top-down view of a connector in an unlocked position on a base according to an embodiment of the present invention.

FIG. 3 shows a top down view of the connector 12 as it rests in an unlocked position on the base 14 according to an embodiment of the present invention. As can be seen in the embodiment of the invention shown in FIG. 3, the illustrated connector 12 includes inner tabs 42 fixedly attached or otherwise extending in a cantilevered fashion from the arms 16. Outer tabs 44 extend, in a cantilevered fashion, from a portion of the connector 12 where the arms 16 extend from the body of the connector 12. The inner tabs 42 and the outer tabs 44 are used to align the connector 12 with the base 44 and lock the connector 12 into place, thereby maintaining the position of the connector 12 with respect to the base 14 as will be explained in greater detail below.

Figure 4:
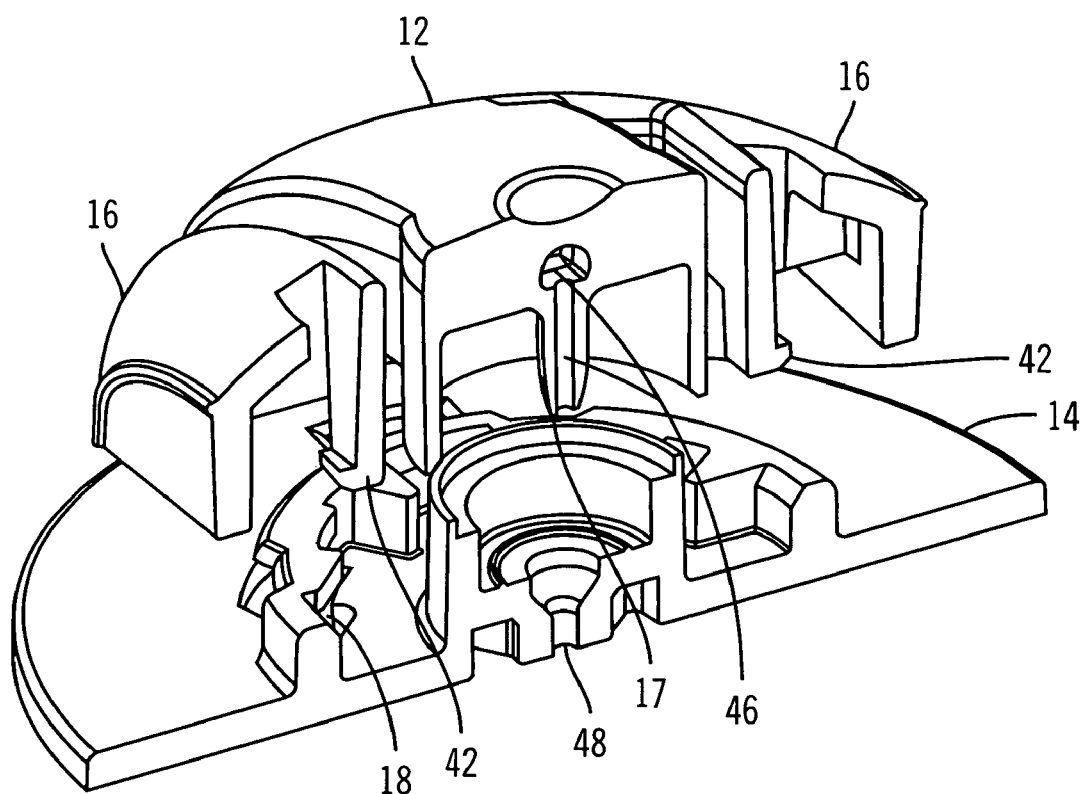
FIG. 4 shows a perspective cutaway view of a connector and a base according to an embodiment of the present invention.

FIG. 4 shows a prospective cutaway view of the connector 12 and the base 14 according to an embodiment of the present invention. As shown in FIG. 4, the inner tabs 42 extend away from the arms 16. When the connector 12 engages the base 14, an inner tab 42 on the connector 12 may be positioned in an inner depression 18 in the base 14. The depression 18 may-be sized liberally, for example, larger than the size of the inner tab 42, so that the inner tab 42 may be easily positioned within it without having to depress the arms 16 on the connector 12.

Also shown in FIG. 4 is a connector duct 46 in a centrally located projection 17 of the connector 12 and a base duct 48 in the base 14. The base duct 48 has a flared or enlarged diameter open-facing toward the connector 12. The connector duct 46 is contiguous with the port 20 (not shown in FIG. 4) and, thus, will pass a fluid, medicant or other infusant when the infusant passes through a tubing into the port 20. When the connector 12 is engaged with the base 14, the connector duct 46 in the projection 17 of the connector 12 extends at least partially into the enlarged or flared end of the base duct 48 to interface with the base duct 48 such that fluid may pass from the connector 12 to and through the base 14. A subcutaneous cannula or catheter (not shown in FIG. 4) may be affixed to the base duct 48 for passing the fluid into the body of a patient.

Figure 5:
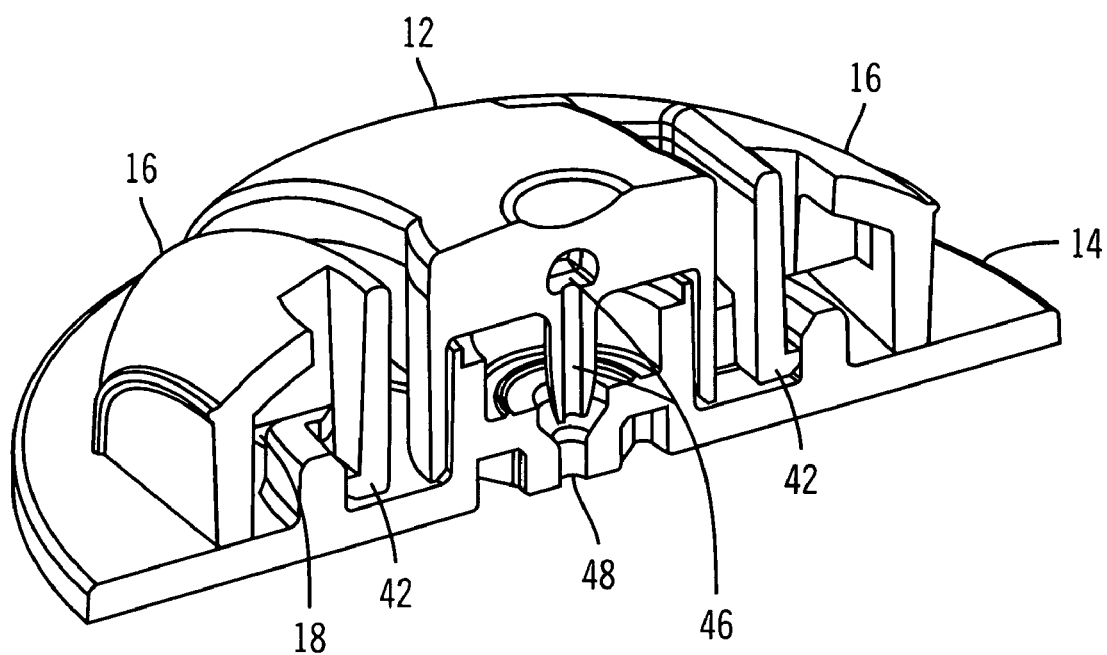
FIG. 5 shows a perspective cutaway view of a connector as it engages a base according to an embodiment of the present invention.

FIG. 5 shows a prospective cutaway view of the connector 12 and the base 14 when the connector 12 is engaged to the base 14 according to an embodiment of the present invention. In FIG. 5, the inner tabs 42 can be seen extending away from the arms 16 and positioned in the depression 18. Moreover, the connector duct 46 can be seen engaging the base duct 48. In FIG. 5, the connector 12 has not been locked onto the base 14 and, thus may be freely removable from the base 14.

Figure 6:
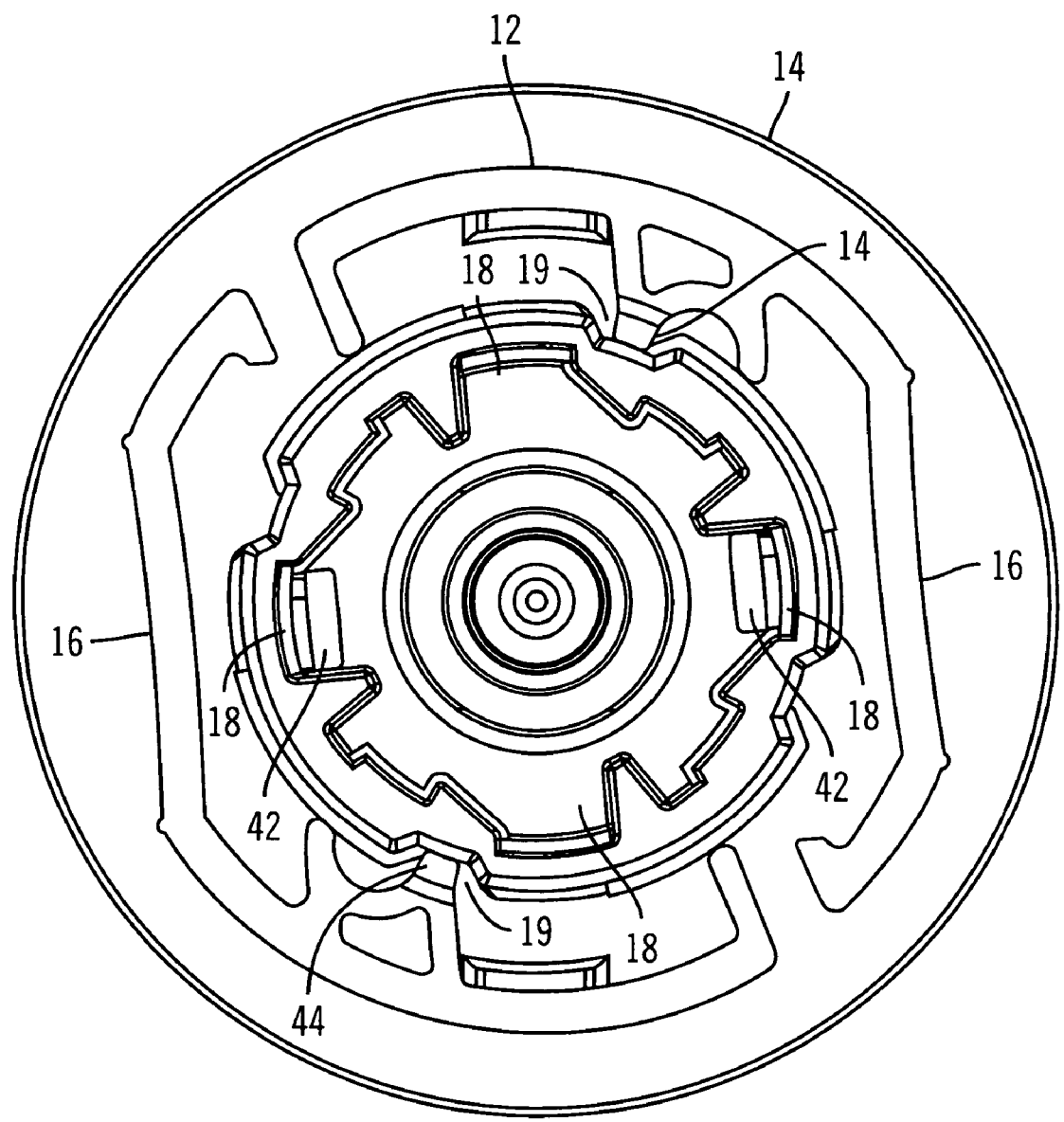
FIG. 6 shows a top-down, skeletal view of a connector as it engages a base in an unlocked position according to an embodiment of the present invention.

FIG. 6 shows a top down, skeletal view of the connector 12 as it engages the base 13 in an unlocked position according to an embodiment of the present invention. As can be seen in the embodiment of the invention shown in FIG. 6, the inner tabs 42 are positioned in the inner depressions 18. In the embodiment of the invention shown in FIG. 6, the connector 12 has two arms 16 and two inner tabs 42. However, the connector 12 may include more than two arms 16 and more than two inner tabs 42. In addition, the base 14 in the embodiment of the invention shown in FIG. 6 includes four inner depressions 18, despite the fact that the connector 12 includes only two inner tabs 42 in the embodiment of the invention shown in FIG. 6. The presence of a plurality of inner depressions 18 allows the connector 12 to engage the base 14 in a plurality of positions. Any number of inner depressions 18 may be configured in the base 14. For example, according to embodiments of the present invention, the base 14 may be configured with two, three, four, five, six or more depressions.

Also shown in the embodiment of the invention of FIG. 6 are outer tabs 44 and outer depressions 19. Much in the same way that the inner tabs 42 are positioned in the inner depressions 18 when the connector 12 engages the base 14, the outer tabs 44 are positioned in the outer depressions 19 when the connector 12 engages the base 14. Both the inner tabs 42 and the outer tabs 44 may be used to guide the connector 12 around the base 14 and to lock the connector 12 to the base 14 as will be explained in greater detail below.

Figure 7:
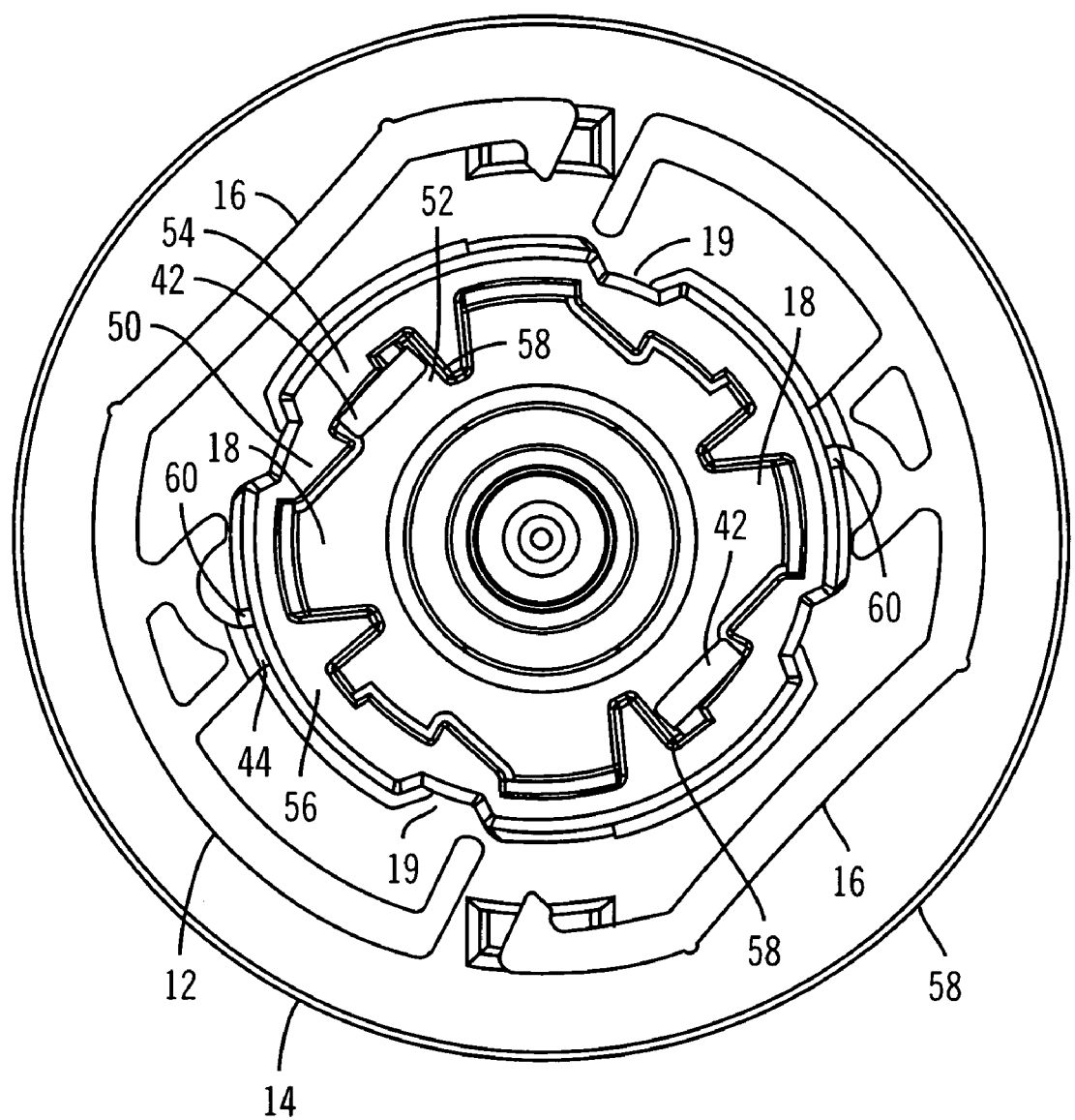
FIG. 7 shows a top-down, skeletal version of a connector as it engages a base in a locked position according to an embodiment of the present invention.

FIG. 7 shows a top down, skeletal version of the connector 12 engaged with the base 14 in a locked position according to an embodiment of the present invention. In the embodiment of the invention shown in FIG. 7, the connector 12 has been rotated from its unlocked position, and, thus, as can be seen in FIG. 7, the inner tabs 42 are no longer disposed in the inner depressions 18. Rather, as the connector 12 has been rotated about the base 13, the inner tab 42 travels radially along the cam 50 and is forced toward the center of the base 14 due to the flexibility of the arm 16. When the connector 12 has been rotated about the base 14 far enough so that the inner tab 42 of the connector 12 reaches the locking depression 52, the inner tab 42 "snaps" into the locking depression 52 of the base 14. An inner underportion 54 is configured such that a portion of the inner tab 42 resides underneath the inner underportion 54, thereby preventing axial movement of the connector 12. The inner tab 42 of the connector 12 is prevented from additional rotation by an inner stop surface 58 and by a proximate end of the cam 50 of the base 14.

Also as the connector 12 is being rotated about the base 14, the outer tab 44 of the connector 12 moves radially along with the connector and is prevented from additional rotation by the second stop surface 60 of the base 14. An outer underportion 56 is configured such that a portion of the outer tab 44 resides underneath the outer underportion 56, thereby preventing axial movement of the connector 12 in the direction of the outer underportion 56 and providing a redundant function of preventing axial movement in addition to that afforded by positioning the inner tab 42 under the inner underportion 54.

Thus, as can be seen in FIG. 7, the connector 12 is in a locked position with respect to the base 14 in a number of respects. The inner tab 42 of the connector 12 is precluded from rotation relative to the base 14 when disposed in the locking depression 52 of the base 14 due to the barriers provided by the cam 50 and the first stop surface 58 of the base 14. Likewise, the outer tab 44 of the connector 12 is precluded from rotation (in the embodiment of the invention shown in FIG. 7, in the clockwise direction) by the second stop surface 60. Additionally, both the inner tab 42 and the outer tab 44 of the connector 12 are prevented from moving axially relative to the base 14 due to the underportions 54 and 56, respectively. Because a portion of the inner tab 42 and the outer tab 44 of the connector 12 reside under the inner underportion 54 and the outer underportion 56, respectively, of the base 14, in that state the connector 12 is effectively precluded from moving away from the base 14. Thus, depression of only one arm 16 is ineffective to remove the connector 12 from the base 14.

In order to remove the connector 12 from the base 14, both arms 16 of the connector 12 may be manually depressed, thereby positioning the inner tabs 42 of the connector 12 away from the locking depressions 52 of the base 14 and removing a portion of the inner tabs 42 from the inner underportions 54 of the base 14. Once the inner tabs 42 have been freed from the locking position due to depression of the arms 16, the connector 12 may be rotated in a direction opposite that used to place the connector 12 in a locking position (in the case of the embodiment of the invention shown in FIG. 7, in a counter-clockwise direction). In the embodiment of the invention shown in FIG. 7, both arms 16 must be depressed in order to free the inner tabs 42 of the connector 12 from the locking depressions 52 of the base 14. When, after rotation, the inner tabs 42 of the connector 12 reach the inner depression 18 of the base 14 and the outer tabs 44 of the connector 12 reach the outer depressions 19 of the base 14, the connector 12 may be removed from the base 14.

Figure 8:
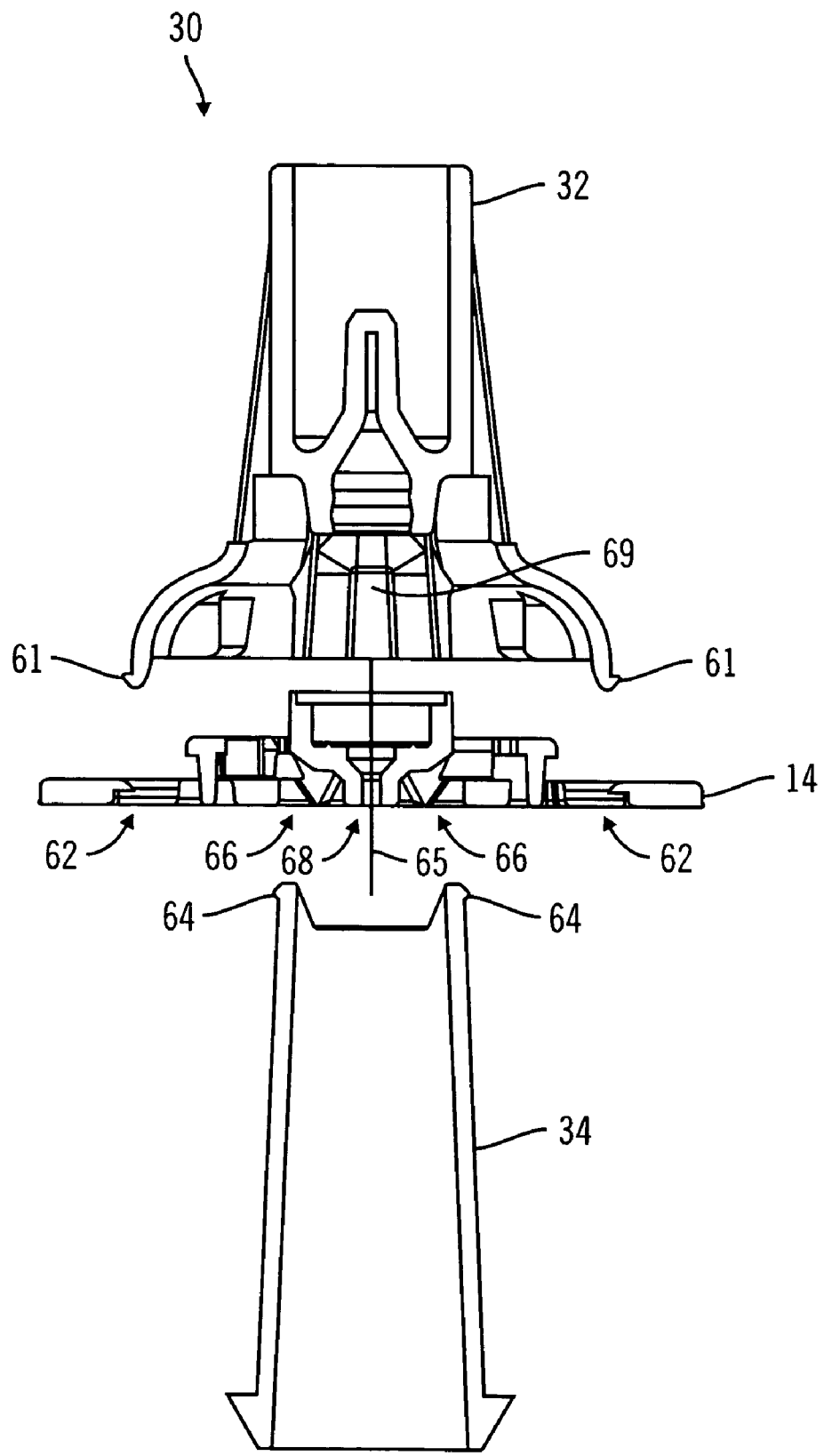
FIG. 8 shows an exploded, cutaway view of an infusion set according to an embodiment of the present invention.

FIG. 8 shows an exploded, cutaway view of the infusion set 30 according to an embodiment of the present invention. In the embodiment of the invention shown in FIG. 8, the hub 32 includes generally rigid hub tabs 61 that have enough flexibility to permit the hub 32 to be removably attached to the base 14 via base apertures 62. Similarly, the guard 34 includes generally rigid guard tabs 64 that have enough flexibility to permit the guard 34 to be removably attached to the base 14 via guard depressions 66. As can also be seen in FIG. 8, the hub 32 may include a hub chamber 69 in which a needle 65 may be affixed. The needle may extend through the base duct 68 and into and through a cannula (not shown) affixed to the base 14 at the opening of the base duct 68. The guard 34 may afford protection from the needle.

Figure 9:
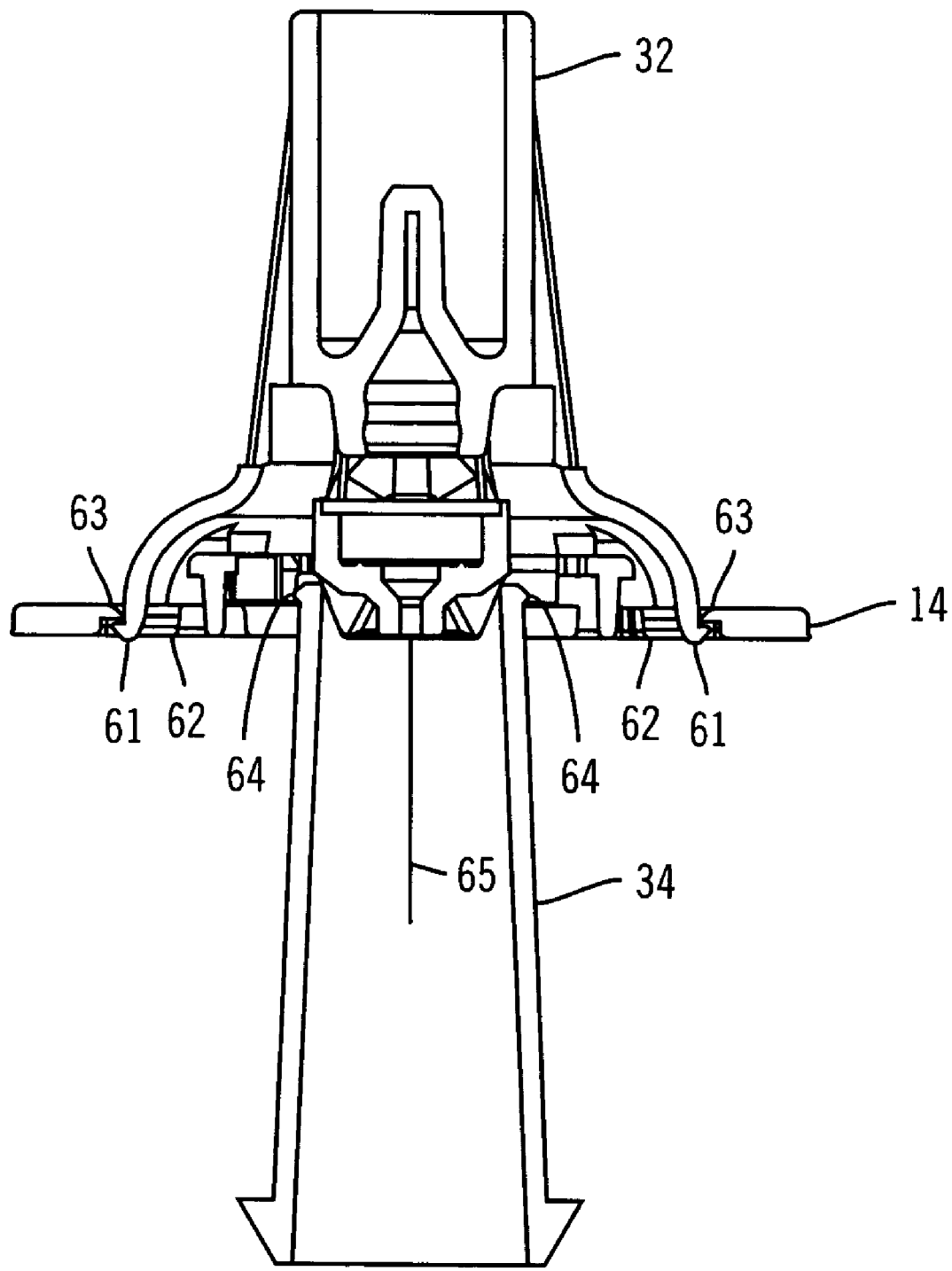
FIG. 9 shows a cutaway view of a hub and a-guard removably attached to a base according to an embodiment of the present invention.

FIG. 9 shows a cutaway view of the hub 32 and guard 34 removably attached to the base 14 according to an embodiment of the present invention. As stated previously, this configuration may be used for storage of the device until a patient is ready to affix the base 14 to the patient's skin. It can be seen in FIG. 9 that the hub tabs 61 have been inserted into the base apertures 62 and are maintained in their position via lips 63 that extend into the base apertures 62. Likewise, the guard tabs 64 have been extended into the guard depressions 66 in the base 14. Both the hub 32 and the guard 34 may be removed from the base 14 by squeezing the body of the hub 32 and the guard 34 in an area close to their respective tabs and separating the hub 32 and the guard 34 from the base 14.

The hub 32 and the guard 34 may also be used together after a patient has positioned the base 14 onto his or her skin. For example, a patient may insert a cannula attached to the base 14 subcutaneously by removing the guard 34 and pushing the needle 65 and cannula into the skin by forcing the hub 32 and the base 14 onto the skin surface while the hub 32 remains affixed to the base 14. However, after subcutaneous insertion of the cannula, the hub 32 may be removed from the base 14, thereby exposing the needle 65 attached to the hub 32. By including apertures (not shown) on the hub 32 configured to accept the guard tabs 64, the guard 34 may be positioned over the needle 65 attached to the hub 32 to protect the patient or anyone else from the needle 65 until the hub 32 can be disposed.

Figure 10:
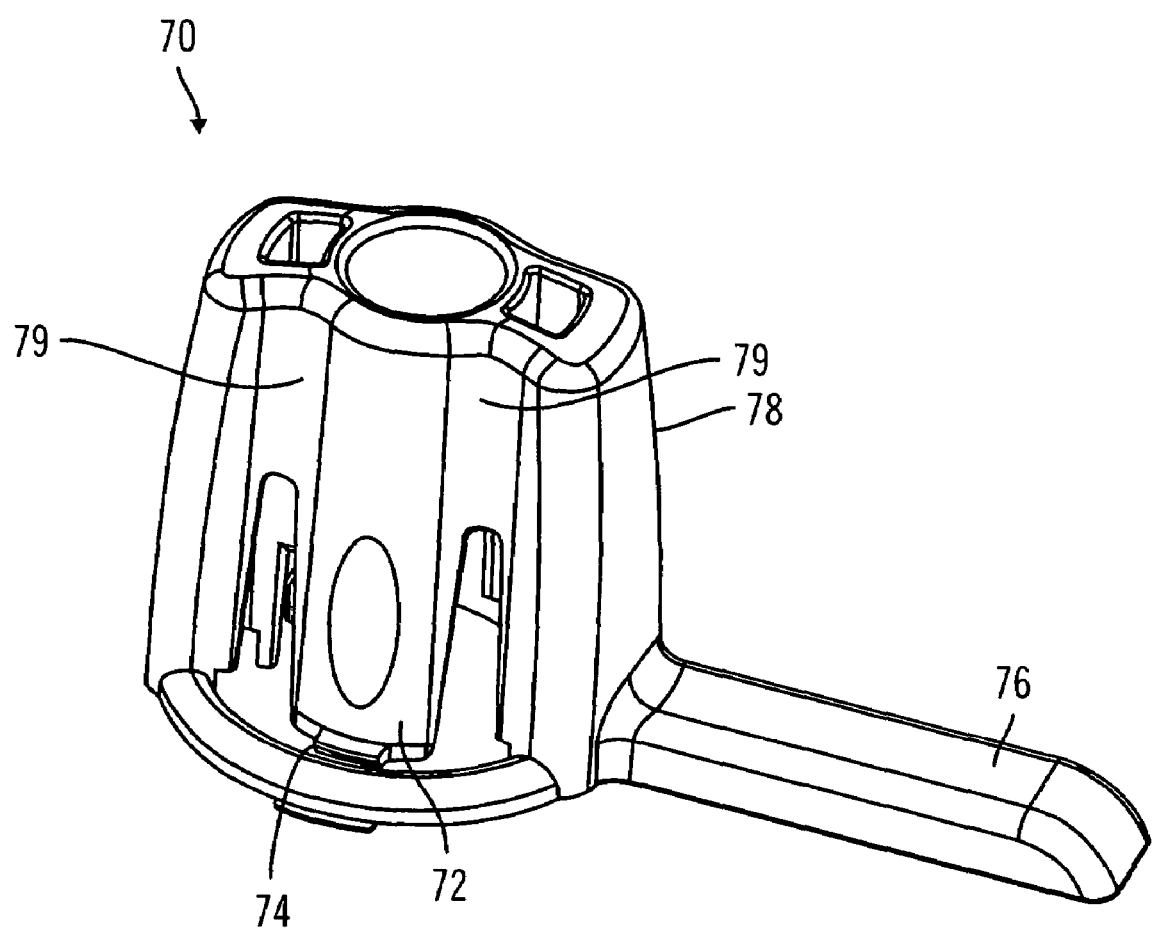
FIG. 10 shows another embodiment of a hub according to an embodiment of the present invention.

FIG. 10 shows another embodiment of a hub 70 according to an embodiment of the present invention. The embodiment of the hub 70 shown in FIG. 10, includes, without limitation, a hub arm 72, a hub tab 74, a hub extension 76 and hub body 78. In FIG. 10, the hub arm 72 has been configured for flexibility, providing adequate movement of the hub tab 74 and allowing for relatively easy application and removal of the hub 70 to a base, such as base 14 described above. In addition, one or more hub tabs 74 may be positioned at the end of a hub arm 72 to lock the hub 70 to a base. The hub extension 76 may be designed with sufficient length to allow a user to hold onto the hub 70 with one hand when using the other hand to remove an insertion tool that may be used with the device or as an aid in positioning the device onto the skin. The hub body 78 may be designed of sufficient size and geometry to allow a user to readily grip and hold onto it, for example, as between a thumb and a forefinger. For example, in the embodiment of the invention shown in FIG. 10, the hub body 78 includes grooves 79 that provide additional friction to a user when holding onto the hub 70.

Figure 11:
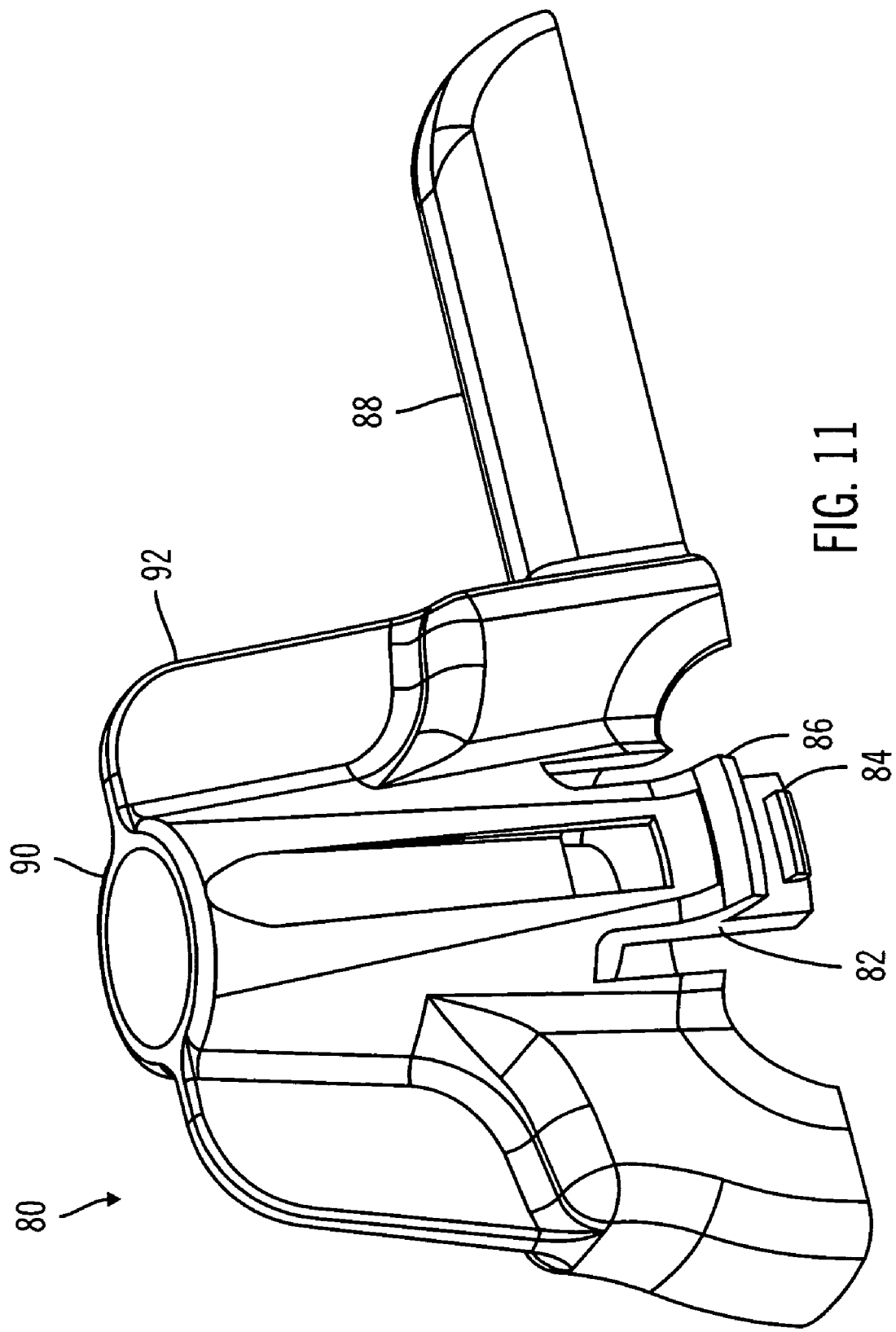
FIG. 11 shows another embodiment of a hub according to an embodiment of the present invention.

FIG. 11 shows another embodiment of a hub 80 according to an embodiment of the present invention. In the embodiment of the invention shown in FIG. 11, the hub 80 includes, without limitation, a hub arm 82, a hub extension 88 and a hub body 90. The hub arm 82 may include one or more hub tabs 84 and a wing 86. The hub tab 84 may be used to lock the hub 80 into a base, such as base 14 described above. The wing 86 may be used to provide additional leverage for a user when inserting the hub 80 onto a base or removing the hub 80 from a base. As can be seen in FIG. 11, the hub arm 82 has been designed to be flexible to allow a user to perform these operations. The hub extension 88 may be designed with sufficient length to allow a user to hold onto the hub 80 when positioning the hub 80 in a base onto the user's skin, for example, with an insertion tool. The hub body 90 may be designed with sufficient size and geometry to allow a user to readily grip and hold onto the hub 80. For example, in the embodiment of the invention shown in FIG. 11, the hub body 90 includes hub flanges 92 with which a user may grab the hub 80, such as, for example, between a thumb and a forefinger.

Figure 12:
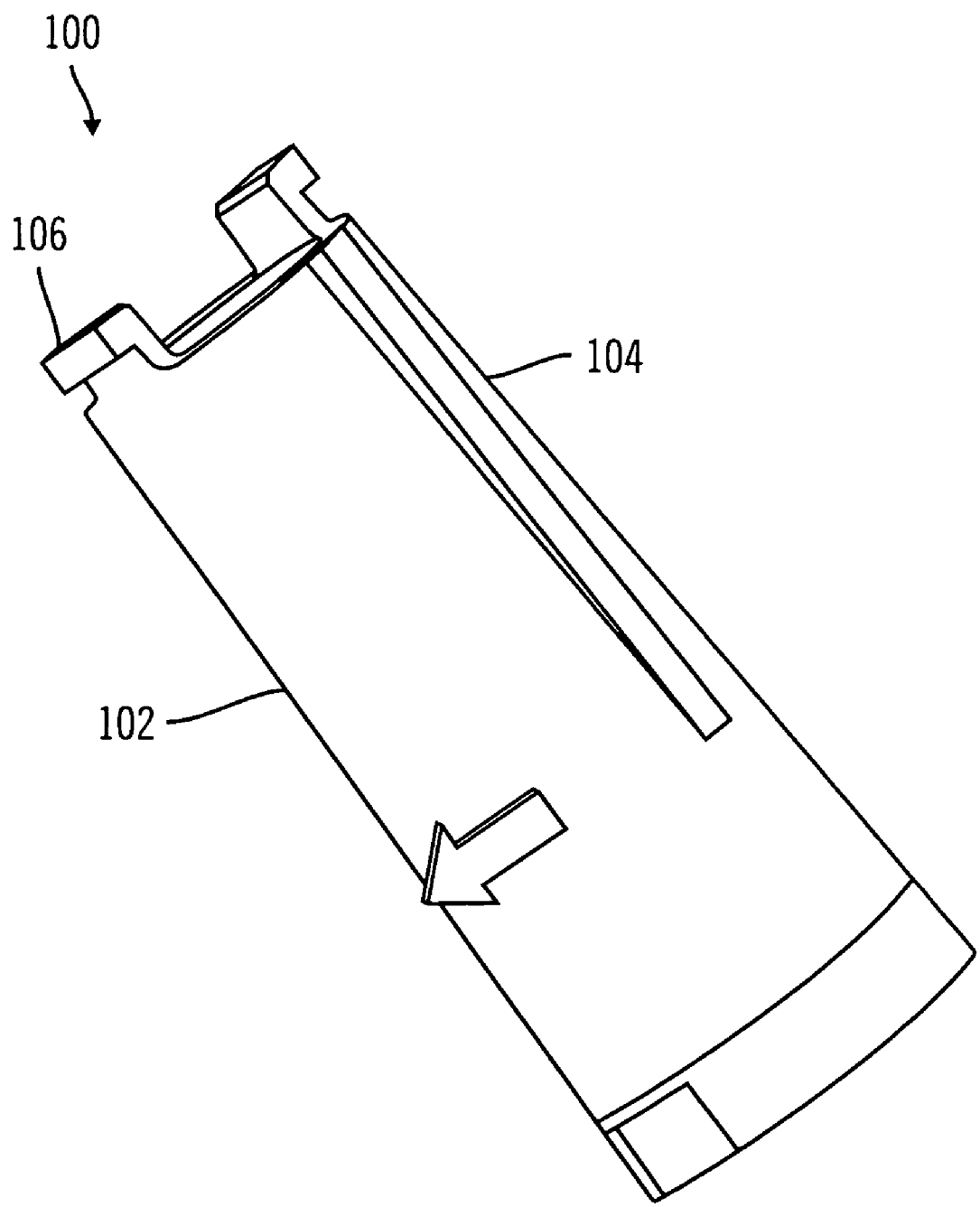
FIG. 12 shows an embodiment of a guard according to an embodiment of the present invention.

FIG. 12 shows an embodiment of a guard 100 according to an embodiment of the present invention. In the embodiment of the invention shown in FIG. 12, the guard 100 may include, without limitation, a body 102, one or more slots 104 and one or more tabs 106. The body 102 may be designed with sufficient size and geometry to enclose a needle or other protrusion which may be extending away from a base or other part of the device. For example, in the embodiment of the invention shown in FIG. 12, the body 102 is substantially cylindrical and has a slight taper. Generally rigid tabs 106 at one end of the body 102 have sufficient flexibility to allow the guard 100 to be removably affixed onto a base or hub as the case may be. The slot 104 facilitates manual "squeezing" of the body 102, thereby making it easier for a user to insert or remove the tabs 106 from a body or a hub.

Figure 13:
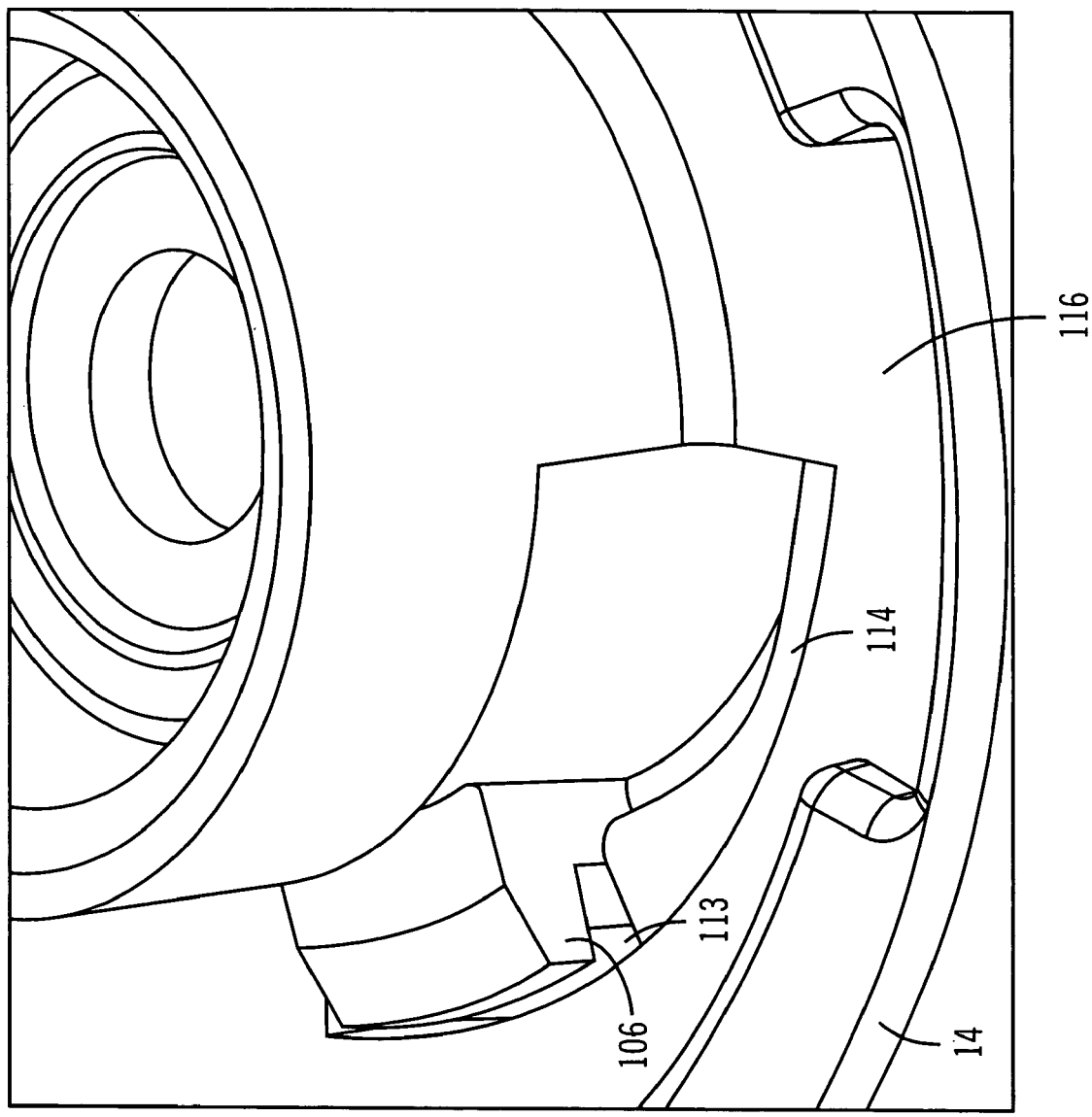
FIG. 13 shows an embodiment of a guard tab interfacing with a base in an unlocked position according to an embodiment of the present invention.

FIG. 13 shows an embodiment of a guard tab 106 interfacing with a base 14 in an unlocked position according to an embodiment of the present invention. In the embodiment of the invention shown in FIG. 13, a guard tab 106 has been inserted into a tab opening 113 on the base 14. The tab opening 113 has been designed for easy insertion of the guard tab 106. The base 14 also includes an underportion 114 which, when the guard tab 106 is rotated away from the tab opening 113, will be positioned underneath a portion of the guard tab 106 and will prevent the guard from being removed from the base.

Figure 14:
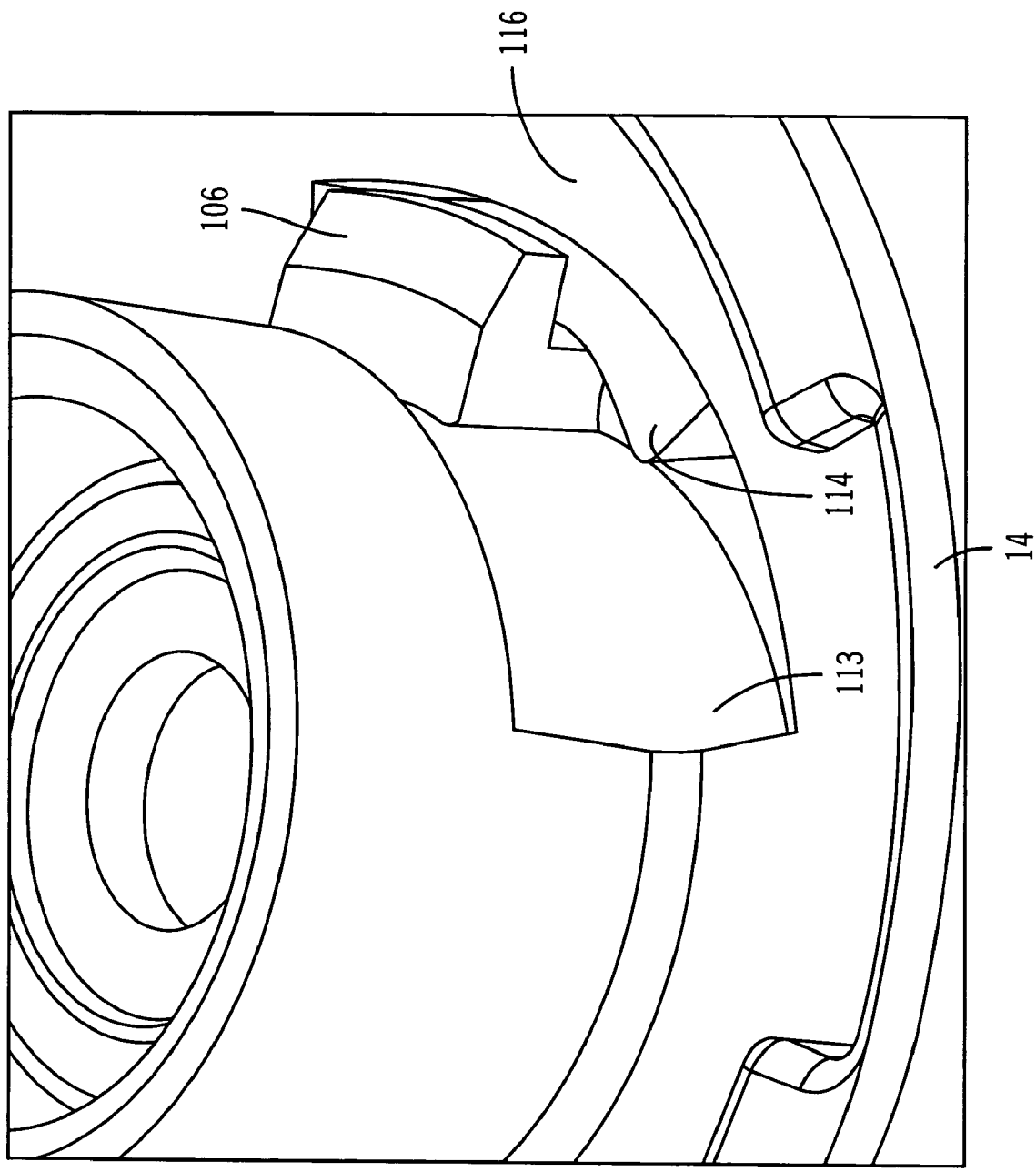
FIG. 14 shows an embodiment of a guard tab interfacing with a base in a locked position according to an embodiment of the present invention.

FIG. 14 shows the guard tab 106 of FIG. 13 in a locked position according to an embodiment of the present invention. In FIG. 14, the guard tab 106 has been rotated over the underportion 114 in the base 14 such that a face of the guard tab 106 engages an edge of the underportion 114. This configuration is possible because the surface of the underportion 114 in the base 14 is lower than the base surface 116. To remove the guard from the base 14 in this embodiment, the guard tab 106 may be rotated toward the tab opening 113, away from the underportion 114 so that a user may pull the guard away from the base 14.

Figure 15:
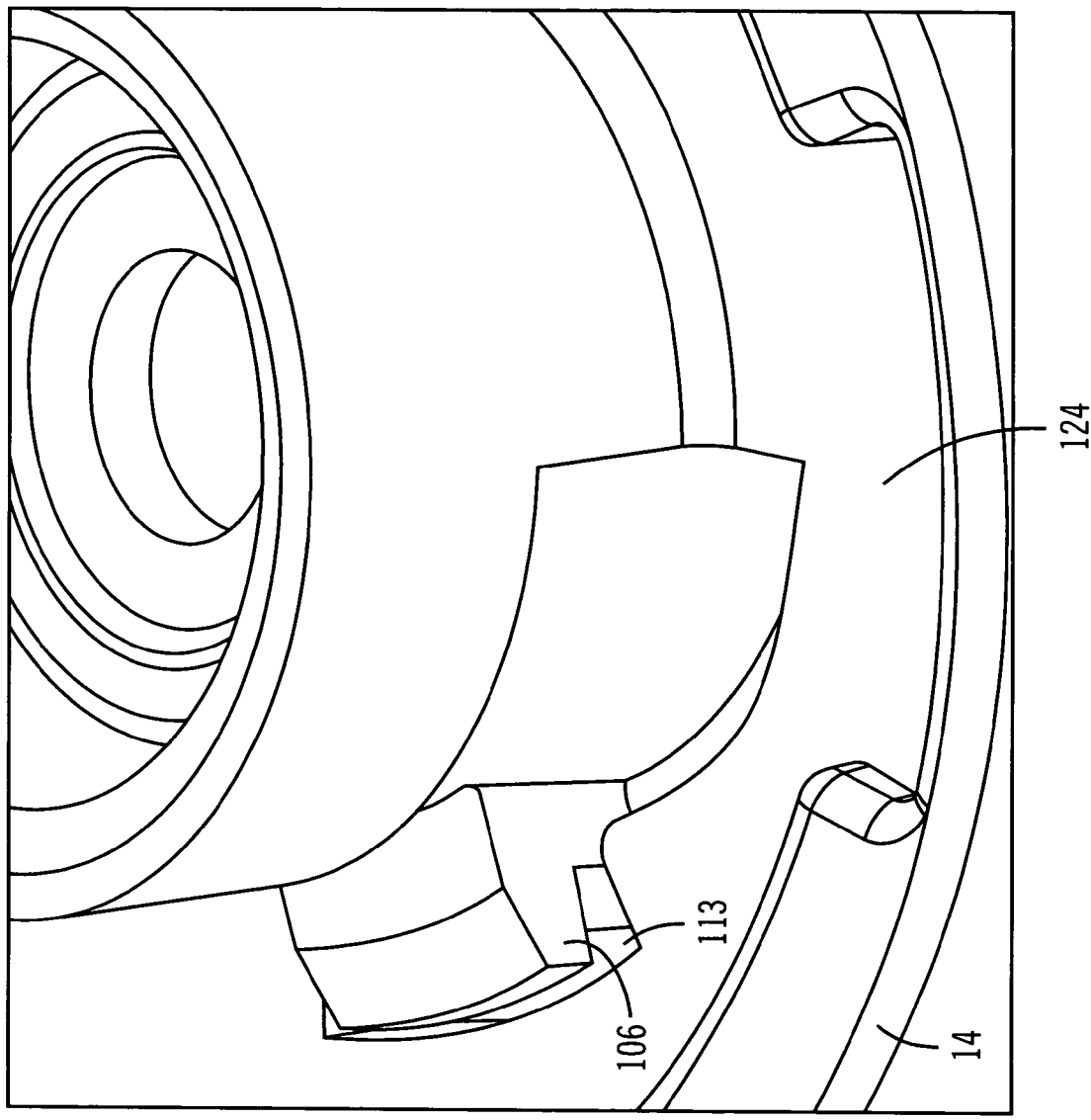
FIG. 15 shows another embodiment of a guard tab interfacing with a base in an unlocked position according to an embodiment of the present invention.
Figure 16:
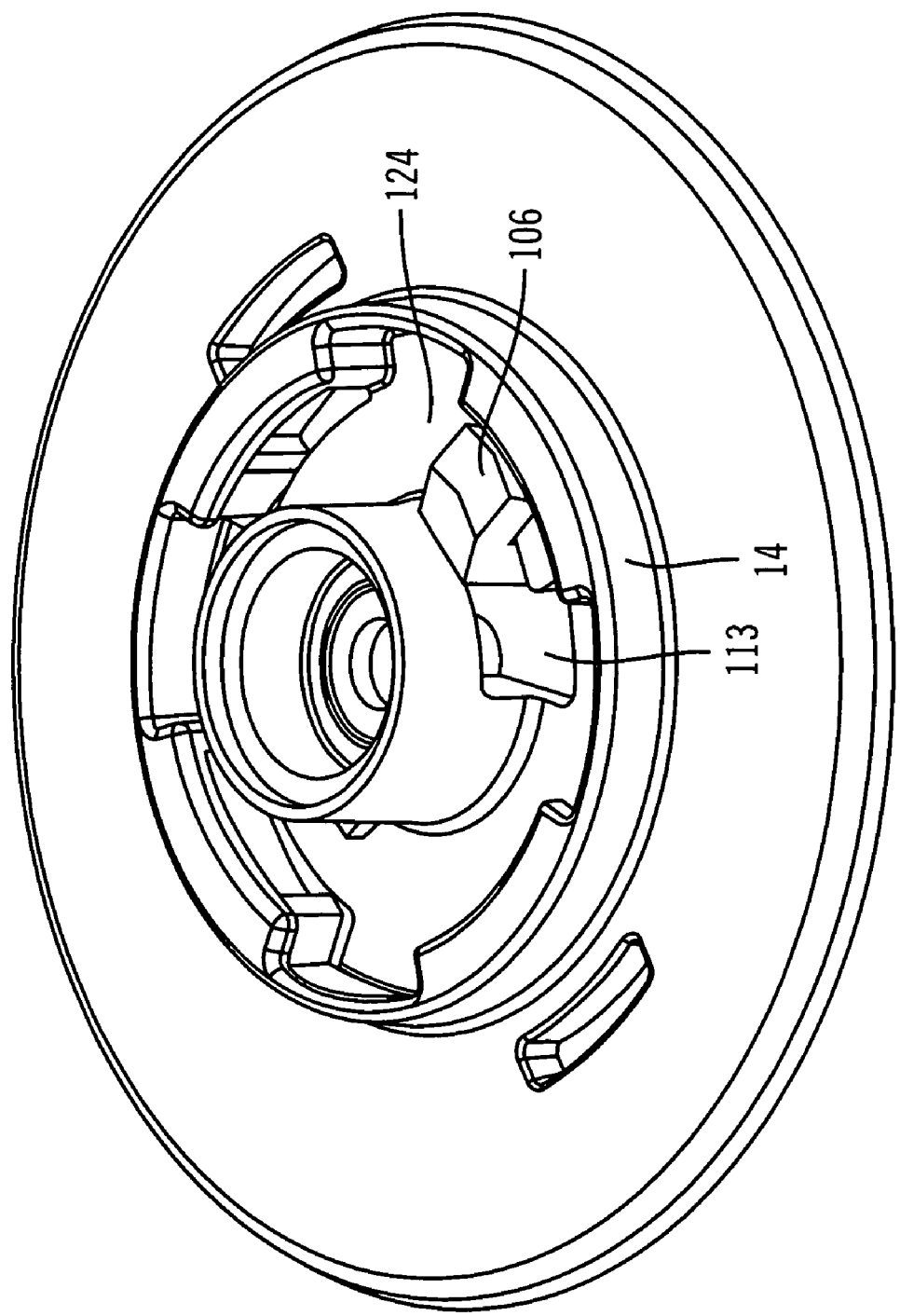
FIG. 16 shows another embodiment of a guard tab interfacing with a base in a locked position according to an embodiment of the present invention.

FIG. 15 shows a guard tab engaging a base according to an embodiment of the present invention. In FIG. 15, the guard tab 106 is positioned in the tab opening 113 of the base 14. In FIG. 15, the guard tab 106 is in an unlocked position in the base 14. In FIG. 16, the guard tab 106 has been rotated about the base surface 124 so that the face of the guard tab 106 rests on an edge of the base surface 124. In this position, the guard tab 106 is locked into the base 14. In the embodiment of the invention shown in FIG. 15 and FIG. 16, the base 14 does not include an underportion and, consequently, the base 14 serves as the mechanism preventing the guard tab 106 from being removed from the base 14.

Figure 17:
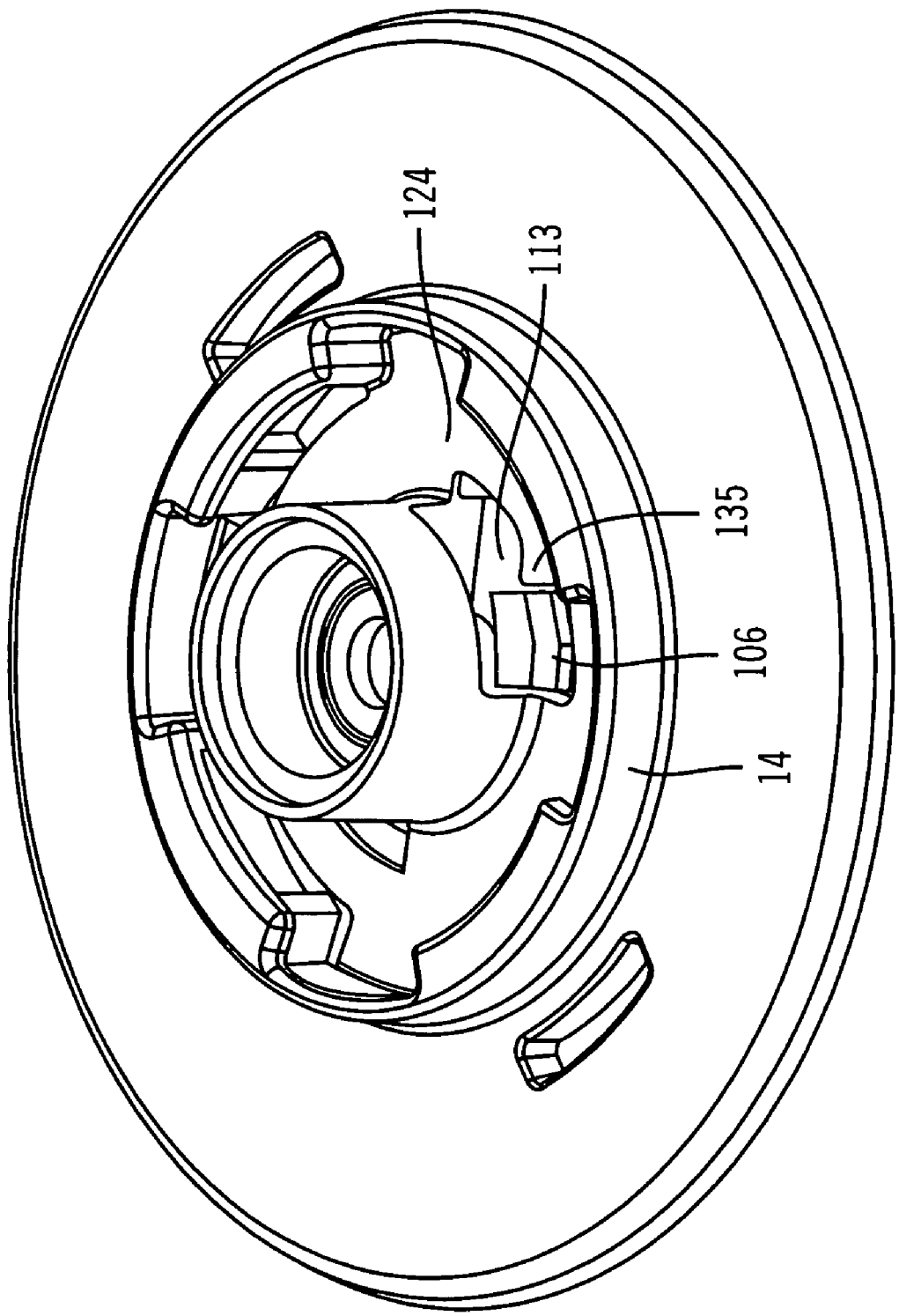
FIG. 17 shows another embodiment of a guard tab interfacing with a base in an unlocked position according to an embodiment of the present invention.
Figure 18:
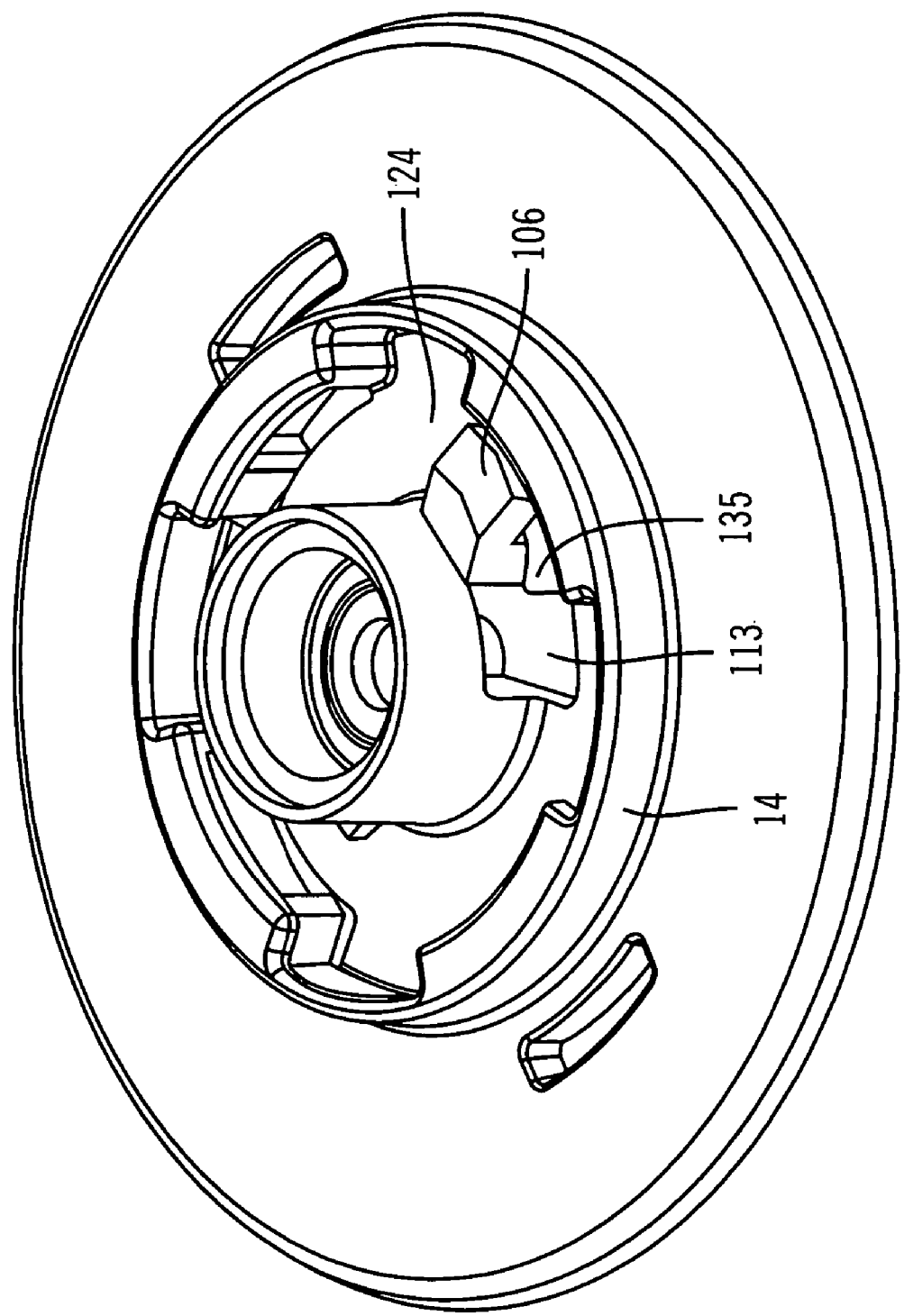
FIG. 18 shows another embodiment of a guard tab interfacing with a base in a locked position according to an embodiment of the present invention.

FIGS. 17 and 18 show a guard tab 106 in locked and unlocked positions, respectively, on a base 14. The guard tab 106 may be rotated from the guard depression 133 so that a face of the guard tab 106 rests on an edge of the base surface 124. In the embodiment of the invention shown in FIGS. 17 and 18, a protrusion 135 on the base surface 124 extends away from the base surface 124 into the space through which the guard tab 106 rotates, requiring an additional active movement by the user, such as, for example, a manual "squeezing" of the guard to move the guard tab 132 from a locked position to an unlocked position and vice versa.

Figure 19:
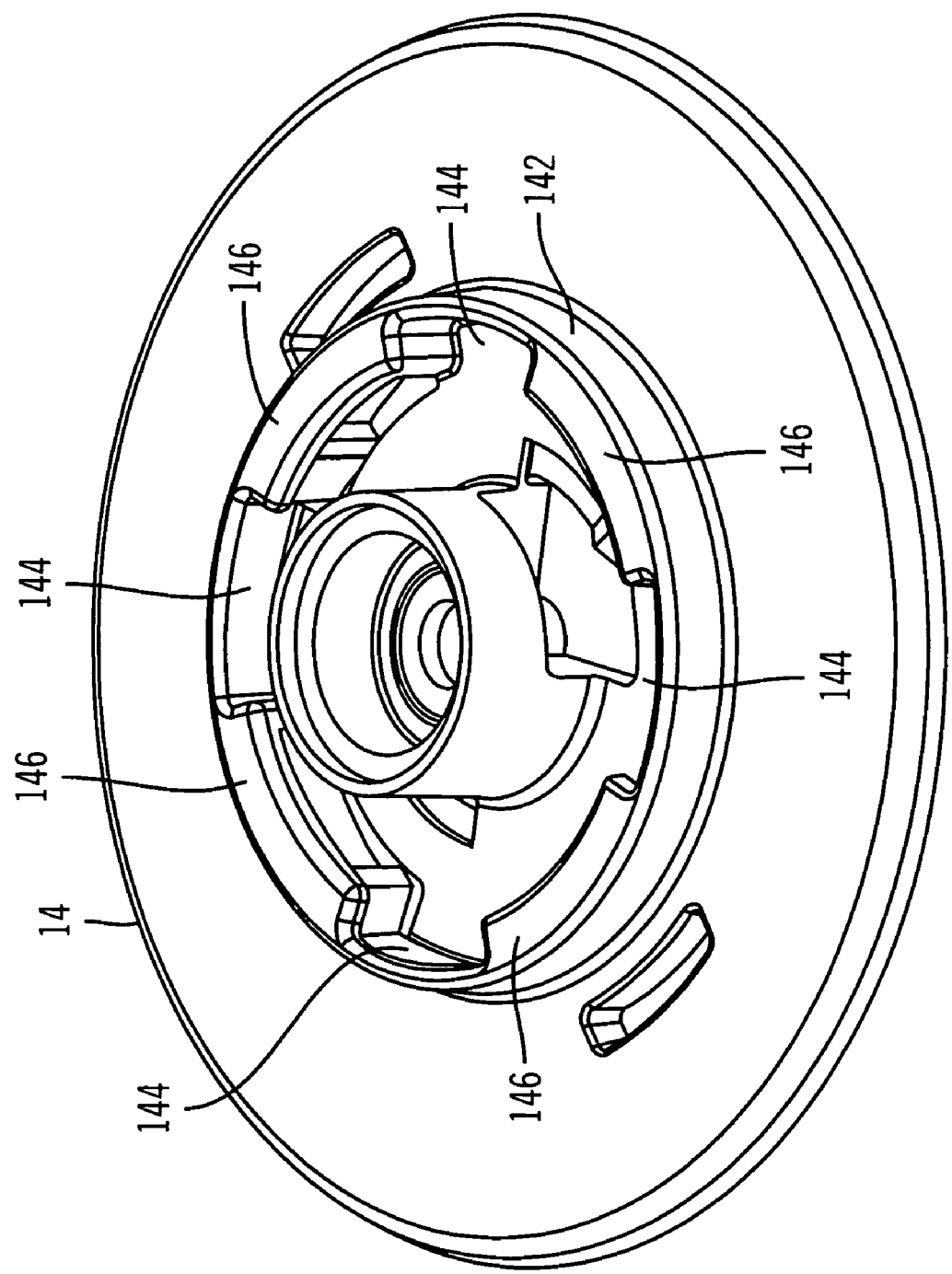
FIG. 19 shows perspective view of another base according to an embodiment of the present invention.

FIG. 19 shows a base 14 according to an embodiment of the present invention. In FIG. 19, the base 14 includes, without limitation, a rim 142, the outside of which is substantially smooth. The rim 142 shown in FIG. 19 is advantageous in that, when the base 14 is positioned on a user's or patient's skin, the smooth outside portion of the rim 142 may minimize the snagging or catching of clothing and the like.

Figure 20:
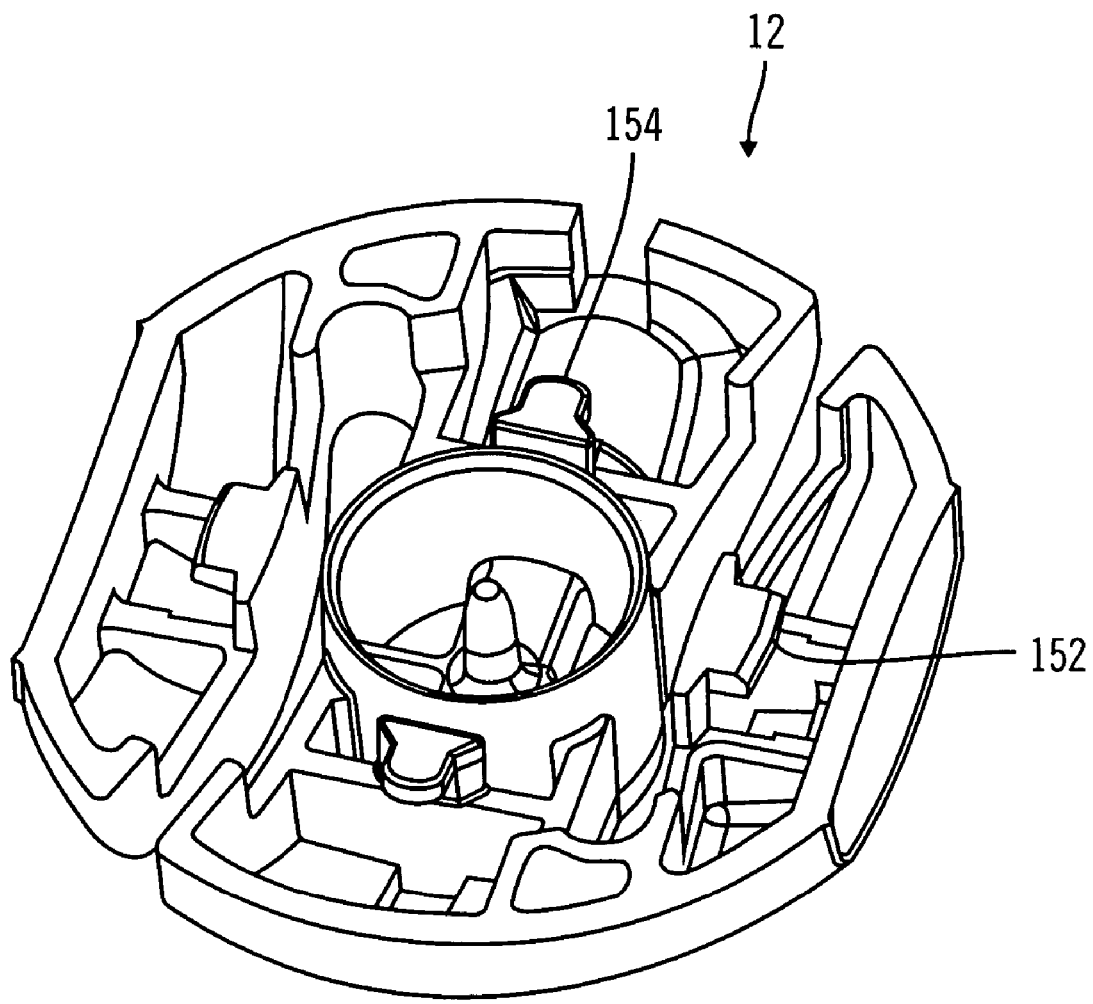
FIG. 20 shows a perspective view of another connector according to an embodiment of the present invention.

FIG. 20 shows a connector 12 suitable for use with a base such as the base 14 shown in FIG. 19 according to an embodiment of the present invention. In FIG. 20, the connector 12 includes flexible tabs 152 and static tabs 154, all of which may be insertable into depressions 144 of the base 14 shown in FIG. 19. Thus, the connector 12 may be positioned onto the base 14 in a plurality of orientations, but, when the connector 12 is rotated such that the flexible tabs 152 and the static tabs 154 are positioned under base edges 146 of the base 14, the connector 12 will be locked onto the base 14.

The flexible tabs 152 and the static tabs 154 may be designed in a variety of ways. For example, in the embodiment of the invention shown in FIG. 20, the flexible tabs 152 have been designed with corners to facilitate locking of the flexible tabs 152 with the base edges 146. However, because the flexible tabs 152 are moveable due to their attachment to the arms of the connector, insertion and removal of the flexible tabs 152 from the base edges 146 is still possible via a positive action by the user. The static tabs 154, on the other hand, are generally not moveable by a user in the embodiment of the invention shown in FIG. 20 and, thus, have been designed with more rounded features to ease engagement with the base edges 146.

While particular embodiments of the present invention have been shown and described, it will be obvious to those skilled in the art that the invention is not limited to the particular embodiments shown and described and that changes and modifications may be made without departing from the spirit and scope of the appended claims.

What is claimed is:

1. An infusion set system comprising:
   a base removably attachable to an infusion site for providing a subcutaneous path in a first generally linear direction for an infusant; and
   a connector removably lockable to the base;
   the connector comprising a connector duct having a fluid flow path that extends in generally the first linear direction and aligns with the linear subcutaneous path upon the connector being locked to the base;
   the connector further comprising a port to which a tubing may be connected in fluid flow communication with the connector duct;
   at least one of the connector and the base further comprising a plurality of tabs;
   at least one of the connector and the base further comprising a plurality of locking surfaces for engaging at least one of the plurality of tabs;
   wherein the connector comprises a single, unitary body in which the connector duct is contiguous with the port for providing a fluid flow connection between the port and the connector duct;
   wherein the base is configured to be engagable by the connector, in a plurality of removably lockable orientations;
   wherein the connector is at least partially rotatable about an axis of the base;
   wherein rotation of the connector about the base causes the at least one of the plurality of tabs to engage with at least one of the plurality of locking surfaces to lock the connector to the base by inhibiting separation of the connector from the base in an axial direction parallel to the axis of the base.

2. The infusion set system of claim 1,
   wherein at least one of the connector and the base further comprises a plurality of apertures, and
   wherein at least one of the plurality of tabs is insertable into the plurality of apertures.

3. The infusion set system of claim 2, wherein at least one tab of the plurality of tabs is flexible.

4. The infusion set system of claim 3, wherein at least one tab of the plurality of tabs is static relative to the connector.

5. The infusion set system of claim 4, wherein at least one flexible tab of the plurality of tabs and at least one static tab of the plurality of tabs are rotatable from an unlocked position within at least one aperture of the plurality of apertures to a locked position.

6. The infusion set system of claim 5, wherein the base comprises a plurality of abutments for locking at least one flexible tab of the plurality of tabs and at least one static tab of the plurality of tabs.

7. The infusion set system of claim 5, wherein the connector comprises a plurality of arms, and wherein each arm of the plurality of arms is fixedly attached to at least one flexible tab of the plurality of tabs.

8. The infusion set system of claim 5, wherein the at least one flexible tab of the plurality of tabs and the at least one static tab of the plurality of tabs are positioned to rotate about the center of the connector.

9. The infusion set system of claim 3, wherein the connector is at least partially rotatable about the base, and wherein at least one tab of the plurality of tabs is rotatable from an unlocked position within at least one aperture of the plurality of apertures to a locked position.

10. The infusion set system of claim 9, wherein the connector comprises a plurality of arms, and wherein each arm of the plurality of arms is fixedly attached to a tab of the plurality of tabs.

11. The infusion set system of claim 10, wherein the plurality of arms are flexible.

12. The infusion set system of claim 11, wherein each arm of the plurality of arms is flexed to remove a tab of the plurality of tabs from the locked position to the unlocked position.

13. The infusion set system of claim 12, wherein the connector is removable from the base by simultaneously flexing the plurality of arms.

14. The infusion set system of claim 9, wherein at least one of the connector and the base further comprises at least one abutment for locking at least one tab of the plurality of tabs into the locked position.

15. The infusion set system of claim 1,
wherein the base includes a cannula for insertion through the infusion site,
wherein the connector includes a tubing for passing the infusant, and
wherein the infusant is subcutaneously passable from the tubing through the cannula when the connector is attached to the base.

16. The infusion set of claim 15, further comprising:
a hub removably attachable to the base, the hub including a needle extending through the base and through the cannula; and
a guard removably attachable to the base opposite the hub for surrounding the needle,
wherein the needle is subcutaneously insertable into the infusion site for subcutaneously positioning the cannula.

17. The infusion set of claim 1, wherein the base includes an adhesive pad for attaching to the infusion site.

18. The infusion set of claim 1, wherein the infusion site is the skin of a patient.

19. An infusion set system as recited in claim 1, wherein the plurality of removably lockable orientations of said connector relative to said base includes at least:
a first orientation in which a port of said connector for passing fluid through the infusion set system faces in a first direction with respect to the base; and
a second orientation in which said port faces in a second direction with respect to the base different from said first direction.

20. The infusion set system of claim 1,
wherein the connector is rotatable at least between a first position and a second position;
wherein the connector is detachable from the base in the first position and the connector is locked in the axial direction to the base to inhibit separation of the connector from the base in the second position; and
wherein the plurality of tabs and the plurality of locking surfaces allow a constant radial motion between the first position and the second position.

21. The infusion set system of claim 1, wherein at least one of the connector and the base is configured to apply a force on at least one of the plurality of tabs when the connector is rotated about the base, the force being directed radially inward toward the axis of the base.

22. A method for assembling an infusant delivery system comprising:
positioning a base at an infusion site for providing a subcutaneous path in a first generally linear direction for the infusant;
engaging the base with a connector in one of a plurality of orientations corresponding to respective ones of a plurality of removably lockable orientations, the connector being removably lockable to the base;
rotating, at least partially, the connector on the base until the connector temporarily locks to the base in one of said removably lockable orientations;
providing the connector with a connector duct having a fluid flow path that extends in generally the first linear direction and aligning the linear subcutaneous path upon the connector being locked to the base;
providing the connector with a port to which a tubing may be connected in fluid flow communication with the connector duct;
providing a plurality of tabs on at least one of the connector and the base; and
providing a plurality of locking surfaces on at least one of the connector and the base for engaging at least one of the plurality of tabs;
wherein providing a the connector with a single, unitary body in which the connector duct is contiguous with the port for providing a fluid flow connection between the port and the connector duct;
wherein the connector is at least partially rotatable about an axis of the base;
wherein rotation of the connector about the base causes the at least one of the plurality of tabs to engage with at least one of the plurality of locking surfaces to lock the connector to the base by inhibiting separation of the connector from the base in an axial direction parallel to the axis of the base.

23. The method of claim 22, wherein at least one of the connector and the base further includes a plurality of apertures.

24. The method of claim 23, further comprising inserting at Least one of the plurality of tabs into the plurality of apertures.

25. The method of claim 24, wherein at least one tab of the plurality of tabs is rotatable from a position within at least one aperture of the plurality of apertures to a locked position.

26. The method of claim 25, further comprising providing at least one abutment on the base for locking at least one tab of the plurality of tabs into a position.

27. The method of claim 23, wherein at least one tab of the plurality of tabs is flexible.

28. The method of claim 27, wherein at least one tab of the plurality of tabs is static relative to the connector.

29. The method of claim 28, wherein at least one flexible tab of the plurality of tabs and at least one static tab of the plurality of tabs are rotatable from an unlocked position within at least one aperture of the plurality of apertures to a locked position.

30. The method of claim 29, further comprising providing a plurality of abutments for locking at least one flexible tab of the plurality of tabs and at least one static tab of the plurality of tabs.

31. The method of claim 29, further comprising providing a plurality of arms, and wherein each arm of the plurality of arms is fixedly attached to at least one flexible tab of the plurality of tabs.

32. The method of claim 29, wherein the at least one flexible tab of the plurality of tabs and the at least one static tab of the plurality of tabs are positioned to rotate about the center of the connector.

33. The method of claim 22, further comprising providing a plurality of arms on the connector, wherein each arm of the plurality of arms is fixedly attached to a tab of the plurality of tabs.

34. The method of claim 33, wherein the plurality of arms are flexible.

35. The method of claim 34, further comprising flexing each arm of the plurality of arms to remove a tab of the plurality of tabs from a locked position to the unlocked position.

36. The method of claim 33, further comprising simultaneously flexing the plurality of arms to remove the connector from the base.

37. The method of claim of claim 22, further comprising inserting a cannula connected to the base through the infusion site, wherein the connector includes a tubing for passing the infusant, and wherein the infusant is subcutaneously passable from the tubing through the cannula when the connector is attached to the base.

38. The method of claim of claim 37, further comprising:
providing a hub removably attachable to the base, the hub including a needle extending through the base and through the cannula;
providing a guard removably attachable to the base opposite the hub for surrounding the needle; and
subcutaneously inserting the needle into the infusion site for subcutaneously positioning the cannula.

39. The method of claim 22, wherein the plurality of removably lockable orientations of said connector relative to said base includes at least:
a first orientation in which a port of said connector for passing fluid through the infusion set system faces in a first direction with respect to the base; and
a second orientation in which said port faces in a second direction with respect to the base different from said first direction.

40. The method of claim 22,
wherein the connector is rotatable at least between a first position and a second position;
wherein the connector is detachable from the base in the first position and the connector is locked in the axial direction to the base to inhibit separation of the connector from the base in the second position; and
wherein the plurality of tabs and the plurality of locking surfaces allow a constant radial motion between the first position and the second position.

41. The method of claim 22, wherein at least one of the connector and the base is configured to apply a force on at least one of the plurality of tabs when the connector is rotated about the base, the force being directed radially inward toward the axis of the base.

42. An infusion set comprising:
a base removably attachable to an infusion site for providing a subcutaneous path in a first generally linear direction for an infusant;
a connector removably attachable to the base;
the connector comprising a connector duct having a fluid flow path that extends in generally the first linear direction and aligns with the linear subcutaneous path upon the connector being locked to the base;
the connector further comprising a port to which a tubing may be connected in fluid flow communication with the connector duct;
wherein the connector comprises a single, unitary body in which the connector duct is contiguous with the port for providing a fluid flow connection between the port and the connector duct; and
at least one of the connector and the base further comprising a locking mechanism for temporarily locking the connector to the base,
wherein the base is engagable by the connector in a plurality of temporarily lockable orientations;
wherein the connector is at least partially rotatable about an axis of the base;
wherein rotation of the connector about the base causes the locking mechanism to temporarily lock the connector to the base by inhibiting separation of the connector from the base in an axial direction parallel to the axis of the base.

43. The infusion set system of claim 42, wherein at least one of the connector and the base further comprises a plurality apertures.

44. The infusion set of claim 43, wherein at least one Of the connector and the base further comprises a plurality of tabs insertable into the plurality of apertures.

45. The infusion set of claim 44, wherein the connector is at least partially rotatable about the base, and wherein at least one tab of the plurality of tabs is rotatable from a position within at least one aperture of the plurality of apertures to a locked position.

46. The infusion set of claim 45, wherein at least one Of the connector and the base comprises at least one abutment for locking at least one tab of the plurality of tabs into a position.

47. The infusion set of claim 45, wherein the connector comprises a plurality of arms, and
wherein each arm of the plurality of arms is fixedly attached to a tab of the plurality of tabs.

48. The infusion set of claim 47, wherein the plurality of arms are flexible.

49. The infusion set of claim 48, wherein each arm of the plurality of arms is flexed to remove a tab of the plurality of tabs from a locked position to the unlocked position.

50. The infusion set of claim 49, wherein the connector is removable from the base by simultaneously flexing the plurality of arms.

51. The infusion set system of claim 44, wherein at least one tab of the plurality of tabs is flexible.

52. The infusion set system of claim 51, wherein at least one tab of the plurality of tabs is static relative to the connector.

53. The infusion set system of claim 52, wherein at least one flexible tab of the plurality of tabs and at least one static tab of the plurality of tabs are rotatable from an unlocked position within at least one aperture of the plurality of apertures to a locked position.

54. The infusion set system of claim 53, wherein the base comprises a plurality of abutments for locking at least one flexible tab of the plurality of tabs and at least one static tab of the plurality of tabs.

55. The infusion set system of claim 53, wherein the connector comprises a plurality of arms, and wherein each arm of the plurality of arms is fixedly attached to at least one flexible tab of the plurality of tabs.

56. The infusion set system of claim 53, wherein the at least one flexible tab of the plurality of tabs and the at least one static tab of the plurality of tabs are positioned to rotate about the center of the connector.

57. The infusion set of claim 42, wherein the base includes a cannula for insertion through the infusion site,
   wherein the connector includes a tubing for passing the infusant, and
   wherein the infusant is subcutaneously passable from the tubing through the cannula when the connector is attached to the base.

58. The infusion set of claim 57, further comprising:
   a hub removably attachable to the base, the hub including a needle extending through the base and through the cannula; and
   a guard removably attachable to the base opposite the hub for surrounding the needle,
   wherein the needle is subcutaneously insertable into the infusion site for subcutaneously positioning the cannula.

59. The infusion set of claim 42, wherein the base includes an adhesive pad for attaching to the infusion site.

60. The infusion set of claim 42, wherein the infusion site is the skin of a patient.

61. An infusion set system as recited in claim 42, wherein the plurality of temporarily lockable orientations of said connector relative to said base includes at least:
   a first orientation in which a port of said connector for passing fluid through the infusion set system faces in a first direction with respect to the base; and
   a second orientation in which said port faces in a second direction with respect to the base different from said first direction.

62. The infusion set system of claim 42,
   wherein the connector is rotatable at least between a first position and a second position;
   wherein the connector is detachable from the base in the first position and the connector is locked in the axial direction to the base to inhibit separation of the connector from the base in the second position; and
   wherein the locking mechanism allows a constant radial motion between the first position and the second position.

63. The infusion set system of claim 42, wherein at least one of the connector and the base is configured to apply a force on the locking mechanism when the connector is rotated about the base, the force being directed radially inward toward the axis of the base.

64. An infusion set comprising:
   base means for positioning at an infusion site to provide a subcutaneous path in a first generally linear direction for an infusant;
   connector means for engaging the base, the connector means being temporarily lockable to the base by rotation of the connector means on the base means until the connector means temporarily locks to the base,
   the connector means for providing a connector duct fluid flow path that extends in generally the first linear direction and aligns with the linear subcutaneous path upon the connector being locked to the base;
   the connector means further comprising providing a port to which a tubing may be connected in fluid flow communication with the connector duct;
   at least one of the connector means and the base means further comprising a plurality of tabs; and
   at least one of the connector means and the base means further comprising a plurality of locking surfaces for engaging at least one of the plurality of tabs;
   wherein the connector means a single, unitary body in which the connector duct is contiguous with the port for providing a fluid flow connection between the port and the connector duct;
   wherein the base means is engagable by the connector means in a plurality of temporarily lockable orientations;
   wherein the connector means is at least partially rotatable about an axis of the base means;
   wherein rotation of the connector means about the base means causes the at least one of the plurality of tabs to engage with at least one of the plurality of locking surfaces to lock the connector means to the base means by inhibiting separation of the connector means from the base means in an axial direction parallel to the axis of the base means.

65. An infusion set system as recited in claim 64, wherein the plurality of temporarily lockable orientations of said connector means relative to said base means includes at least:
   a first orientation in which a port of said connector means for passing fluid through the infusion delivery system faces in a first direction with respect to the base means; and
   a second orientation in which said port faces in a second direction with respect to the base means different from said first direction.

66. The infusion set system of claim 64,
   wherein the connector means is rotatable at least between a first position and a second position;
   wherein the connector means is detachable from the base means in the first position and the connector means is locked in the axial direction to the base means to inhibit separation of the connector means from the base means in the second position; and
   wherein the plurality of tabs and the plurality of locking surfaces allow a constant radial motion between the first position and the second position.

67. The infusion set system of claim 64, wherein at least one of the connector means and the base means is configured to apply a force on at least one of the plurality of tabs when the connector means is rotated about the base means, the force being directed radially inward toward the axis of the base means.

* * * * *